US007789847B2

(12) United States Patent
Gibbs et al.

(10) Patent No.: US 7,789,847 B2
(45) Date of Patent: Sep. 7, 2010

(54) METHODS AND APPARATUS FOR LEUKOREDUCTION OF RED BLOOD CELLS

(75) Inventors: Bruce W. Gibbs, Arvada, CO (US); Jon Herskovits, Aurora, CO (US)

(73) Assignee: CaridianBCT, Inc., Lakewood, CO (US)

( * ) Notice: Subject to any disclaimer, the term of this patent is extended or adjusted under 35 U.S.C. 154(b) by 0 days.

(21) Appl. No.: 11/842,479

(22) Filed: Aug. 21, 2007

(65) Prior Publication Data

US 2007/0282242 A1 Dec. 6, 2007

Related U.S. Application Data

(62) Division of application No. 11/278,884, filed on Apr. 6, 2006, which is a division of application No. 10/316,753, filed on Dec. 10, 2002, now Pat. No. 7,052,606.

(60) Provisional application No. 60/339,653, filed on Dec. 10, 2001.

(51) Int. Cl.
*A61M 37/00* (2006.01)
(52) U.S. Cl. .............. 604/6.03; 604/6.09; 604/6.01; 604/6.02; 604/6.11; 604/6.15; 604/4.01; 604/5.01; 210/645; 210/647; 210/649; 210/651; 210/782; 210/646; 210/648; 422/44
(58) Field of Classification Search .............. 604/6.03, 604/6.09, 6.01, 6.02, 6.11, 6.15, 4.01, 5.01; 210/645, 647, 649, 651, 782, 646, 648; 422/44
See application file for complete search history.

(56) References Cited

U.S. PATENT DOCUMENTS 4,177,149 A 12/1979 Rosenberg
(Continued)

FOREIGN PATENT DOCUMENTS

EP 0852151 A1 * 7/1998
(Continued)

OTHER PUBLICATIONS

International Search Report for PCT/US02/39590.
(Continued)

*Primary Examiner*—Tatyana Zalukaeva
*Assistant Examiner*—Ginger T Chapman
(74) *Attorney, Agent, or Firm*—Laura B. Arciniegas; John R. Merkling; Edna M. O'Connor

(57) ABSTRACT

A method and apparatus for red blood collection and filtration is provided wherein a red blood cell collection assembly provides for leukoreduction filtration concurrent with or soon after the red blood cell separation and collection procedure. Such procedures involve filtering the separated red blood cells in a diluted state after and/or prior to flushing the filter with storage solution. Storage solution may thus be passed through the leukoreduction filter before, with and/or after the RBCs have been filtered therethrough. The red blood cell collection, filtration and storage assembly is preferably pre-connected to a blood component separation disposable assembly, including, for example, a centrifuge vessel and a blood removal/return assembly for removing blood from a donor, passing the blood to the centrifuge vessel for separation of the blood into components for collection and providing for filtration of the separated red blood cell component.

12 Claims, 14 Drawing Sheets

U.S. PATENT DOCUMENTS

| | | | |
|---|---|---|---|
| 4,197,847 A * | 4/1980 | Djerassi | 604/6.02 |
| 4,360,435 A * | 11/1982 | Bellamy et al. | 210/636 |
| 4,400,277 A | 8/1983 | Leason | |
| 4,596,657 A * | 6/1986 | Wisdom | 210/206 |
| 4,680,025 A | 7/1987 | Kruger et al. | |
| 4,701,267 A | 10/1987 | Watanabe et al. | |
| 4,767,541 A | 8/1988 | Wisdom | |
| 4,810,378 A | 3/1989 | Carmen et al. | |
| 4,855,063 A | 8/1989 | Carmen et al. | |
| 4,880,548 A | 11/1989 | Pall et al. | |
| 4,915,848 A | 4/1990 | Carmen et al. | |
| 4,919,823 A | 4/1990 | Wisdom | |
| 4,923,620 A | 5/1990 | Pall | |
| 4,925,572 A | 5/1990 | Pall | |
| 4,936,998 A | 6/1990 | Nishimura et al. | |
| 4,943,287 A * | 7/1990 | Carmen | 604/408 |
| 4,985,153 A * | 1/1991 | Kuroda et al. | 210/782 |
| 4,997,577 A | 3/1991 | Stewart | |
| 5,009,654 A * | 4/1991 | Minshall et al. | 604/410 |
| 5,089,146 A | 2/1992 | Carmen et al. | |
| 5,092,996 A | 3/1992 | Spielberg | |
| 5,100,551 A | 3/1992 | Pall et al. | |
| 5,100,564 A | 3/1992 | Pall et al. | |
| 5,104,788 A | 4/1992 | Carmen et al. | |
| 5,126,054 A | 6/1992 | Matkovich | |
| 5,152,905 A | 10/1992 | Pall et al. | |
| 5,180,504 A | 1/1993 | Johnson et al. | |
| 5,217,627 A | 6/1993 | Pall et al. | |
| 5,229,012 A | 7/1993 | Pall et al. | |
| 5,236,716 A | 8/1993 | Carmen et al. | |
| 5,252,222 A | 10/1993 | Matkovich et al. | |
| 5,258,126 A | 11/1993 | Pall et al. | |
| 5,258,127 A | 11/1993 | Gsell et al. | |
| 5,269,946 A | 12/1993 | Goldhaber et al. | |
| 5,281,342 A | 1/1994 | Biesel et al. | |
| 5,300,060 A | 4/1994 | Nelson | |
| 5,302,299 A | 4/1994 | Pascale et al. | |
| 5,316,674 A | 5/1994 | Pall et al. | |
| 5,344,561 A | 9/1994 | Pall et al. | |
| 5,360,545 A | 11/1994 | Pall et al. | |
| 5,362,406 A | 11/1994 | Gsell et al. | |
| 5,364,526 A | 11/1994 | Matkovich et al. | |
| 5,399,268 A | 3/1995 | Pall et al. | |
| 5,403,272 A | 4/1995 | Deniega et al. | |
| 5,427,695 A * | 6/1995 | Brown | 210/805 |
| 5,431,814 A | 7/1995 | Jorgensen | |
| 5,445,736 A | 8/1995 | Pall et al. | |
| 5,451,321 A | 9/1995 | Matkovich | |
| 5,470,488 A | 11/1995 | Matkovich et al. | |
| 5,472,621 A | 12/1995 | Matkovich et al. | |
| 5,501,795 A | 3/1996 | Pall et al. | |
| 5,512,187 A | 4/1996 | Buchholz et al. | |
| 5,527,472 A | 6/1996 | Bellotti et al. | |
| 5,536,238 A | 7/1996 | Bischof | |
| 5,543,062 A | 8/1996 | Nishimura | |
| 5,545,339 A | 8/1996 | Bormann et al. | |
| 5,547,591 A | 8/1996 | Hagihara et al. | |
| 5,549,834 A | 8/1996 | Brown | |
| 5,580,465 A | 12/1996 | Pall et al. | |
| 5,587,070 A | 12/1996 | Pall et al. | |
| 5,601,730 A | 2/1997 | Page et al. | |
| 5,607,579 A * | 3/1997 | Latham et al. | 210/195.1 |
| 5,616,254 A | 4/1997 | Pall et al. | |
| 5,630,946 A | 5/1997 | Hart et al. | |
| 5,670,060 A | 9/1997 | Matkovich et al. | |
| 5,674,173 A | 10/1997 | Hlavinka et al. | |
| 5,690,815 A | 11/1997 | Krasnoff et al. | |
| 5,695,653 A | 12/1997 | Gsell et al. | |
| 5,722,926 A | 3/1998 | Hlavinka et al. | |
| 5,738,796 A | 4/1998 | Bormann et al. | |
| 5,744,047 A | 4/1998 | Gsell et al. | |
| 5,762,791 A | 6/1998 | Deniega et al. | |
| 5,769,839 A | 6/1998 | Carmen et al. | |
| 5,863,436 A | 1/1999 | Matkovich | |
| 5,865,785 A | 2/1999 | Bischof | |
| 5,879,318 A * | 3/1999 | Van Der Heiden et al. | 604/6.02 |
| 5,902,490 A | 5/1999 | Zuk, Jr. | |
| 5,906,570 A | 5/1999 | Langley et al. | |
| 5,913,768 A | 6/1999 | Langley et al. | |
| 5,939,319 A | 8/1999 | Hlavinka et al. | |
| 5,948,278 A | 9/1999 | Sammons et al. | |
| 5,951,877 A | 9/1999 | Langley et al. | |
| 5,954,971 A | 9/1999 | Pages et al. | |
| 6,030,539 A | 2/2000 | Zuk, Jr. | |
| 6,051,147 A | 4/2000 | Bischof | |
| 6,053,856 A | 4/2000 | Hlavinka | |
| 6,053,885 A | 4/2000 | Beshel | |
| 6,071,421 A * | 6/2000 | Brown | 210/782 |
| 6,071,422 A | 6/2000 | Hlavinka et al. | |
| 6,080,322 A * | 6/2000 | Deniega et al. | 210/739 |
| 6,200,287 B1 | 3/2001 | Keller et al. | |
| 6,334,842 B1 | 1/2002 | Hlavinka et al. | |
| 6,354,986 B1 | 3/2002 | Hlavinka et al. | |
| 6,361,692 B1 | 3/2002 | Bischof | |
| 6,495,039 B1 | 12/2002 | Lee et al. | |
| 6,709,412 B2 | 3/2004 | Vandlik et al. | |
| 6,872,307 B2 | 3/2005 | Bischof | |
| 7,052,606 B2 | 5/2006 | Gibbs et al. | |
| 7,651,474 B2 * | 1/2010 | Van Waeg et al. | 604/6.16 |
| 2002/0090319 A1 * | 7/2002 | Vandlik et al. | 422/44 |
| 2004/0236263 A1 * | 11/2004 | Van Waeg et al. | 604/5.01 |

FOREIGN PATENT DOCUMENTS

| | | | |
|---|---|---|---|
| WO | WO 01/24848 | * | 4/2001 |
| WO | WO 01/36022 | * | 5/2001 |
| WO | WO 01/66172 | * | 9/2001 |

OTHER PUBLICATIONS

Nossaman, Janis, Implementation of the COBE R\LS Pre-storage.

* cited by examiner

METHODS AND APPARATUS FOR LEUKOREDUCTION OF RED BLOOD CELLS

CROSS-REFERENCE TO RELATED APPLICATIONS

This Application is a divisional of U.S. application Ser. No. 11/278,884 filed Apr. 6, 2006 which is a divisional of U.S. application Ser. No. 10/316,753, filed on Dec. 10, 2002, which claims priority to U.S. provisional application Ser. No. 60/339,653, filed Dec. 10, 2001, which is incorporated herein by reference in its entirety to the extent not inconsistent herewith.

FIELD OF INVENTION

The present invention relates generally to the field of extracorporeal blood processing methods and apparatus which are particularly useful in blood component collection, and more particularly, the present invention relates to methods and apparatus for the leukoreduction of red blood cells preferably collected with an apheresis system.

BACKGROUND OF THE INVENTION

One well-known type of extracorporeal blood processing involves an apheresis system and/or procedure in which blood is removed from a donor or a patient (hereafter cumulatively referred to as a donor), directed to a blood component separation device (e.g., centrifuge), and separated into various blood component types (e.g., red blood cells, white blood cells, platelets, plasma) for collection or therapeutic purposes. One or more or all of these blood component types may either be collected, and/or treated for therapeutic purposes before storage or return to a patient, while the remainder may simply be returned to the donor or patient. One such system is one in which only a particular component of interest, such as red cells, is collected with all other blood component types being returned to the donor.

A number of factors may affect the commercial viability of an apheresis system. One factor relates to the time and/or expertise required of an individual to prepare and operate the apheresis system. For instance, reducing the time required by the operator to complete an entire collection procedure, as well as reducing the complexity of these actions, can increase productivity and/or lower the potential for operator error. Moreover, reducing the dependency of the system on the operator may further lead to reductions in the credentials desired/required for the operators of these systems.

Donor-related factors may also impact the commercial viability of an apheresis system and include, for example, donor convenience and donor comfort. For instance, donors/patients may have a limited amount of time which may be committed to a donation or therapeutic procedure. Consequently, once at the collection or treatment facility, the amount of time which is actually spent collecting and/or treating blood components is an important consideration. This also relates to donor comfort as the actual collection procedure may be somewhat discomforting because at least one and sometimes two access needles are disposed in the donor throughout the procedure.

Performance-related factors also affect the commercial viability of an apheresis system. Performance may be judged in terms of the collection efficiency of the apheresis system, which may impact or improve product quality and/or may in turn reduce the amount of processing time and thus decrease operator burden and increase donor convenience. The collection efficiency of a system may of course be gauged in a variety of ways, such as by the amount of a particular blood component type which is collected in relation to the quantity of this blood component type which passes through the apheresis system. Performance may also be evaluated based upon the effect which the apheresis procedure has on the various blood component types. For instance, it is desirable to minimize the adverse effects on the blood component types as a result of the apheresis procedure (e.g., reduce platelet activation).

Another performance-related factor is the end quality of the collected blood component. For example, if red blood cells are the component to be collected, it is generally desirable that such red blood cells be leukoreduced by the removal of white blood cells or leukocytes. White blood cells can present problems to the ultimate recipient of the collected blood component. Transfused products containing white blood cells can provoke immunogenic reactions and viral diseases. Conventionally, filters have been used to remove leukocytes from collected blood products or components. For example, U.S. Pat. No. 5,954,971 discloses the use of a filter with an apheresis system for filtering a diluted blood component prior to collection. Other distinctive methods have also been used, and these have generally dictated special preliminary steps such as pre-chilling and/or overnight storage of collected components prior to filtration. Another distinct conventional filtration step is the venting or air handling/recirculation or by-passing at the end of the filtration procedure which had been deemed important for substantial recovery of a remainder portion of the blood component to be processed through a red blood cell filter. Another technique used for leukoreduction is the technique of actively pumping the red blood cells through the leukoreduction filter. Such active pumping, however, may result in cell damage and thus affect the end quality of the collected component.

An apparatus and method for red blood cell filtration in conjunction with apheresis separation is also disclosed in the commonly-owned U.S. Patent Applications, Ser. No. 09/672,519, filed Sep. 27, 2000; and Ser. No. 09/714,390, filed Nov. 16, 2000; the disclosures hereof being incorporated by reference herein as if fully set forth. Further background on apheresis red blood cell separation and collection can be found in the PCT publication WO99/11305, which is also incorporated herein by this reference.

SUMMARY OF THE INVENTION

The present invention generally relates to extracorporeal blood processing. Since each of the various aspects of the present invention may preferably be incorporated into an apheresis system (e.g., whether for blood component collection in which "healthy" cells or other blood components are removed from the donor blood for later transfusion, or for therapeutic "unhealthy" blood component removal), the present invention will be described in preferred relation to such apheresis systems. Apheresis may often imply the return of certain blood components back to the donor. However certain aspects of the present invention may be suited for extracorporeal blood processing applications in which all donated blood components are retained and such are also intended within the scope of the present invention.

An apheresis system which may be used with and/or in one or more aspects of the present invention generally includes at least a blood component separation device (e.g., a membrane-based separation device, and/or a rotatable centrifuge element, such as a rotor and channel combination), which provides the mechanism and/or the forces required to separate blood into its various blood component types (e.g., red blood cells, white blood cells, platelets, and/or plasma). In one preferred embodiment, the separation device includes a centrifuge channel which receives a disposable blood processing vessel. Typically, a donor or perhaps a patient (collectively referred to hereafter as a donor) is fluidly interconnected with the blood processing vessel by an extracorporeal tubing circuit, and preferably the blood processing vessel and extracorporeal tubing circuit collectively define a closed, sterile system. When the fluid interconnection is established, blood may be extracted from the donor or patient and directed to the blood component separation device such that at least one type of blood component may be separated and removed from the blood, either for collection or for therapy.

One aspect of the present invention relates to an extracorporeal blood processing device which is used to provide leukoreduced red blood cells, that in one embodiment includes a disposable assembly which may include one or more flexible tubing lines adjacently interconnected to a blood processing vessel, a collection container interconnected to one of the flexible tubing lines, and a filtration device for filtering a selected separated blood component type such as separated red blood cells. The filtration device is preferably disposed between the blood processing vessel and the collection container. In one embodiment, multiple sets of corresponding first and second tubing lines and collection containers are provided, with each of the sets providing for selective collection of a blood component in a separate collection container or for diversion back to the donor. Use of such an arrangement yields a compact disposable assembly that can be readily mounted relative to the blood component separation machine in a reliable manner. The tubing lines may also be interconnected to a disposable cassette member.

Another aspect of the present invention relates to the extracorporeal separation and collection of red blood cells using an apheresis blood processing system. More particularly, a method for such separation and collection includes separating high hematocrit red blood cells from the blood within a blood processing vessel of a blood component separation machine and collecting at least a portion of the separated red blood cells within a red blood cell collection container that is disparate from yet preconnected via tubing lines to the blood processing vessel. Such red blood cells may be separated and collected alone, or prior or subsequent to or concurrently with other blood components such as platelets and/or plasma. According to the present invention, before the ultimate collection of the red blood cells in the collection container, the red blood cells are filtered through a filtration device. This filtration preferably occurs during the overall separation procedure, although it could be initiated soon after and as part of the commencement of the collection procedure. Nevertheless, the separation procedure may be a continuous or batch process, and in either case, the filtration occurs upon or soon after removal of the separated high hematocrit red blood cells from the processing vessel, yet preferably concurrently with or soon after the overall separation process. In a continuous separation process, this red blood cell filtration can be continually performed during the continual separation and removal of the separated red blood cells from the processing vessel. In this context, the word "after" means only post-separation in the separation vessel; it does not mean that the entire separation process must be completed prior to filtration.

A further aspect of the invention relates to an apheresis disposable assembly including a leukoreduction filter for filtering the red blood cell component to be collected. In conjunction with this aspect, the instant invention provides a preconnected disposable assembly comprising a separation vessel for separating blood into components, a fluid flow cassette with internal passageways and a leukoreduction filter for filtering separated red blood cells upon or soon after removal of those red blood cells from the separation vessel yet preferably concurrently with or soon after the overall separation process. As above, the adverbial modifier "after" is intended to mean only post-separation, not requiring the entire overall separation process to be complete.

Still one further aspect of the present invention relates to a method for using a preconnected disposable assembly which includes a leukoreduction filter. This method generally involves pushing separated red blood cells through the filter within a short time period after separation of the red blood cells from donor blood. In one embodiment, the separated red blood cells are passively pushed through the filter. Another aspect of this method includes the option of rinsing or flushing an additive or storage solution through the leukoreduction filter before flowing the red blood cells through the filter, and/or with the red blood cells during filtration thereof and/or after completion of the red blood cell filtration through the leukoreduction filter.

In another aspect, the separated red blood cells may be filtered in a high hematocrit state as they exist after separation in the apheresis system. Here also, filtration may take place during or soon after the overall apheresis process. As above, the phrase "after separation" here does not require completion of the entire separation process. An additive/storage solution may be and preferably is added to the red blood cells before and/or during and/or after such filtration. The additive/storage solution may thus also be flushed through the filter after the red blood cells are filtered therethrough. In one embodiment the additive/storage solution is pushed through the filter, in another it is gravity fed to the filter, and in yet another embodiment it may be pumped via a discrete pump therethrough. Alternative systems for pressurizing the storage solution may be used and may particularly include a valve and an optional flow meter or fluid detector so as to provide the desired proportionate flow of storage solution for the red blood cells being collected.

These and still further aspects of the present invention are more particularly described in the following description of the preferred embodiments presented in conjunction with the attached drawings which are described briefly below.

DETAILED DESCRIPTION

The present invention will be described in relation to the accompanying drawings which assist in illustrating the pertinent features hereof. Generally, the primary aspects of the present invention relate to both procedural and structural improvements in or a sub-assembly for use with a blood apheresis system. However, certain of these improvements may be applicable to other extracorporeal blood processing applications whether any blood components are returned directly to the donor or otherwise; and such are within the scope of the present invention as well.

Figure 1:
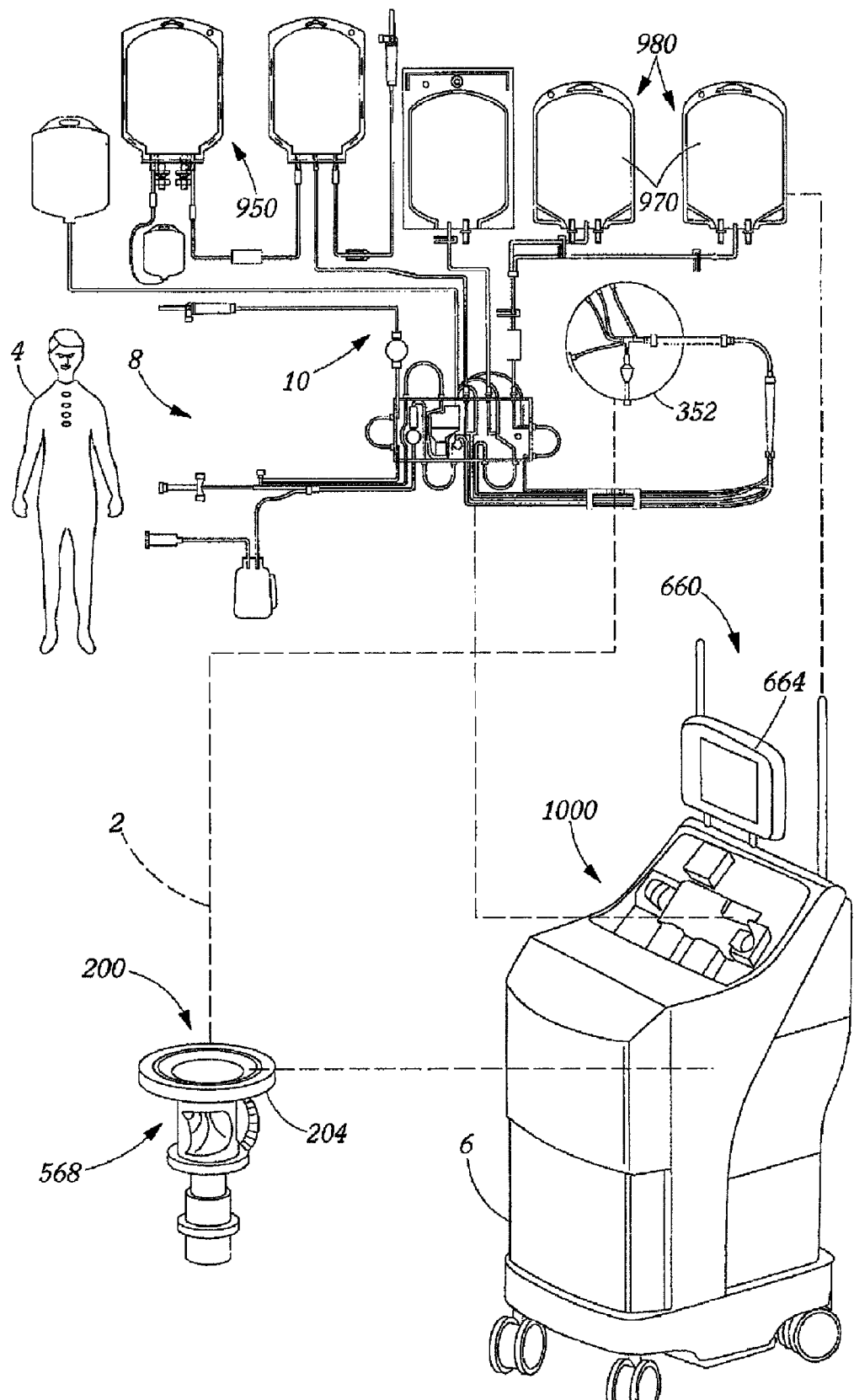
FIG. 1 is a schematic view of one embodiment of an apheresis system which can be used in or with the present invention.

A preferred blood apheresis system 2 for use in and/or with the present invention is schematically illustrated in FIG. 1. System 2 preferably provides for a continuous blood component separation process. Generally, whole blood is withdrawn from a donor 4 and is substantially continuously provided to a blood component separation device 6 where the blood is continuously separated into various component types and at least one of these blood component types is preferably continuously collected from the device 6. One or more of the separated blood components may then either be provided for collection and subsequent use by another through transfusion or may be uncollected and then returned to the donor 4. Therapeutic treatment and near immediate return of certain separated blood components is a viable, yet less common alternative use hereof as well. It is also understood that for therapeutic treatment the blood may be separated into components with filtration using the principles of the instant invention and as described below at a patient's bedside for return to such patient.

In the blood apheresis system 2, blood is withdrawn from the donor 4 and directed through a preconnected bag and tubing set 8 which includes an extracorporeal tubing circuit 10 and, in one embodiment, a blood processing vessel 352 which together define a closed, sterile and disposable system. The set 8 is preferably disposable and is adapted to be mounted on and/or in the blood component separation device 6. The separation device 6 preferably includes a pump/valve/sensor assembly 1000 for interfacing with the extracorporeal tubing circuit 10, and a channel assembly 200 for interfacing with the disposable blood processing vessel 352.

The channel assembly 200 may include a channel housing 204 which is rotatably interconnected with a rotatable centrifuge rotor assembly 568 which provides the centrifugal forces required to separate blood into its various blood component types by centrifugation. The blood processing vessel 352 may then be interfitted within the channel housing 204. When thus connected as described, blood can then be flowed substantially continuously from the donor 4, through the extracorporeal tubing circuit 10, and into the rotating blood processing vessel 352. The blood within the blood processing vessel 352 may then be continuously separated into various blood component types and at least one of these blood component types (e.g., platelets, plasma, or red blood cells) is preferably continually removed from the blood processing vessel 352. Blood components which are not being retained for collection or for therapeutic treatment (e.g., platelets and/or plasma) are preferably also removed from the blood processing vessel 352 and returned to the donor 4 via the extracorporeal tubing circuit 10. Note, various alternative apheresis systems (not shown) may also make use of the present invention; including batch processing systems (non-continuous inflow of whole blood and/or non-continuous outflow of separated blood components) or smaller scale batch or continuous RBC/plasma separation systems, whether or even if no blood components may be returned to the donor.

Operation of the blood component separation device 6 is preferably controlled by one or more processors included therein, and may advantageously comprise a plurality of embedded computer processors to accommodate interface with ever-increasing PC user facilities (e.g., CD ROM, modem, audio, networking and other capabilities). Relatedly, in order to assist the operator of the apheresis system 2 with various aspects of its operation, the blood component separation device 6 preferably includes a graphical interface 660 preferably with an interactive touch screen 664.

Further details concerning the operation of a preferred apheresis system, such as the Gambro Trima® System and the Trima® Accel™ System (available from a related company to the assignee of this application, Gambro BCT, Inc., Lakewood, Colo.) may be found in a plurality of publications, including, for example, WO99/11305 and U.S. Pat. Nos. 5,653,887; 5,676,644; 5,702,357; 5,720,716; 5,722,946; 5,738,644; 5,750,025; 5,795,317; 5,837,150; 5,919,154; 5,921,950; 5,941,842; and 6,129,656; among numerous others. The disclosures hereof are incorporated herein as if fully set forth. A plurality of other known apheresis systems may also be useful herewith, as for example, the Baxter CS3000® and/or Amicus® and/or Autopheresis-C® and/or Alyx systems, and/or the Haemonetics MCS® or MCS®+ and/or the Fresenius COM.TEC™ or AS-104™ and/or like systems.

Disposable Set: Extracorporeal Tubing Circuit

Figure 2:
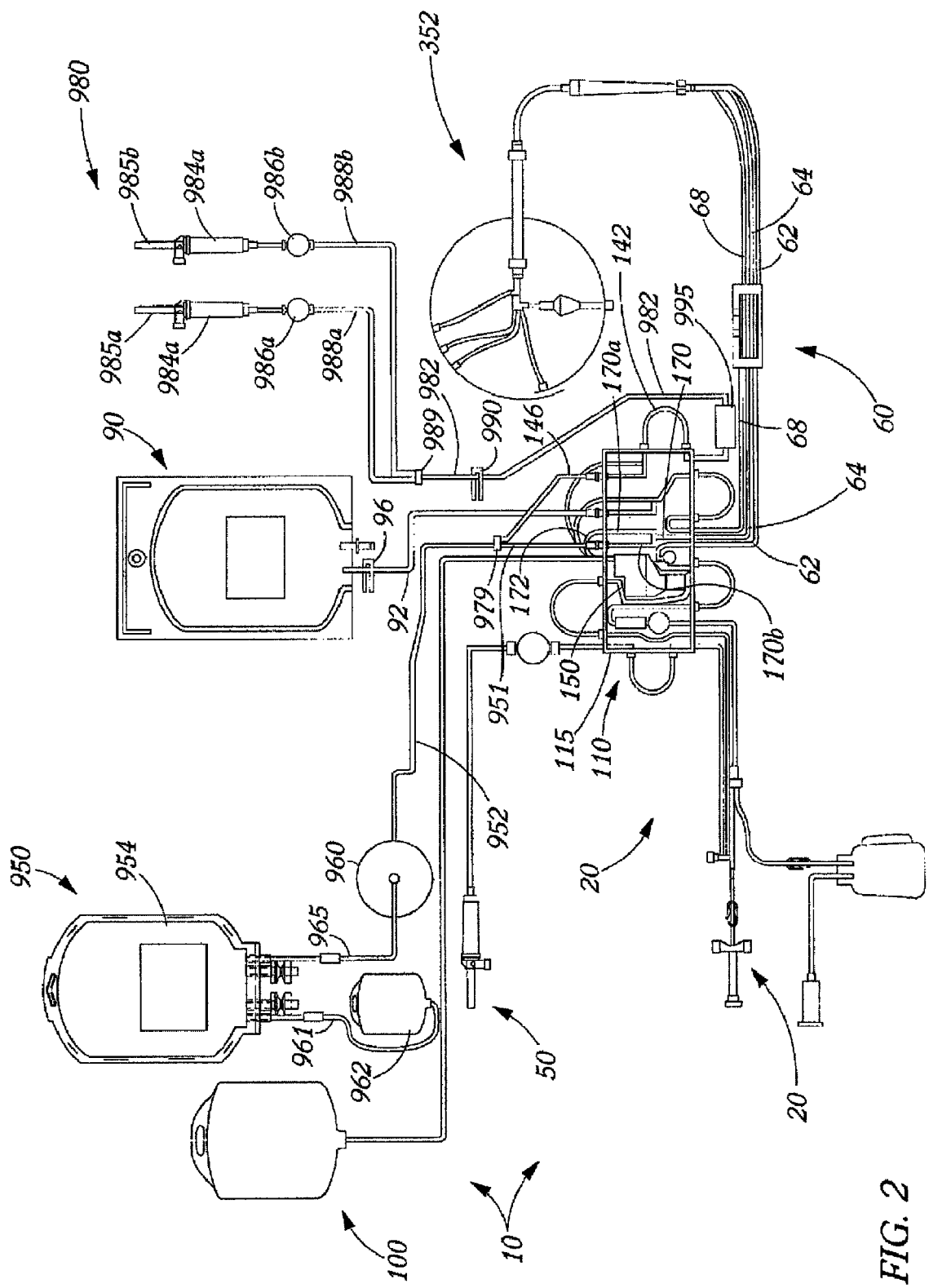
FIG. 2 illustrates a tubing and bag set including an extracorporeal tubing circuit, a cassette assembly, and a filter and collection bag assembly for use in or with the system of FIG. 1 pursuant to the present invention.
Figure 3:
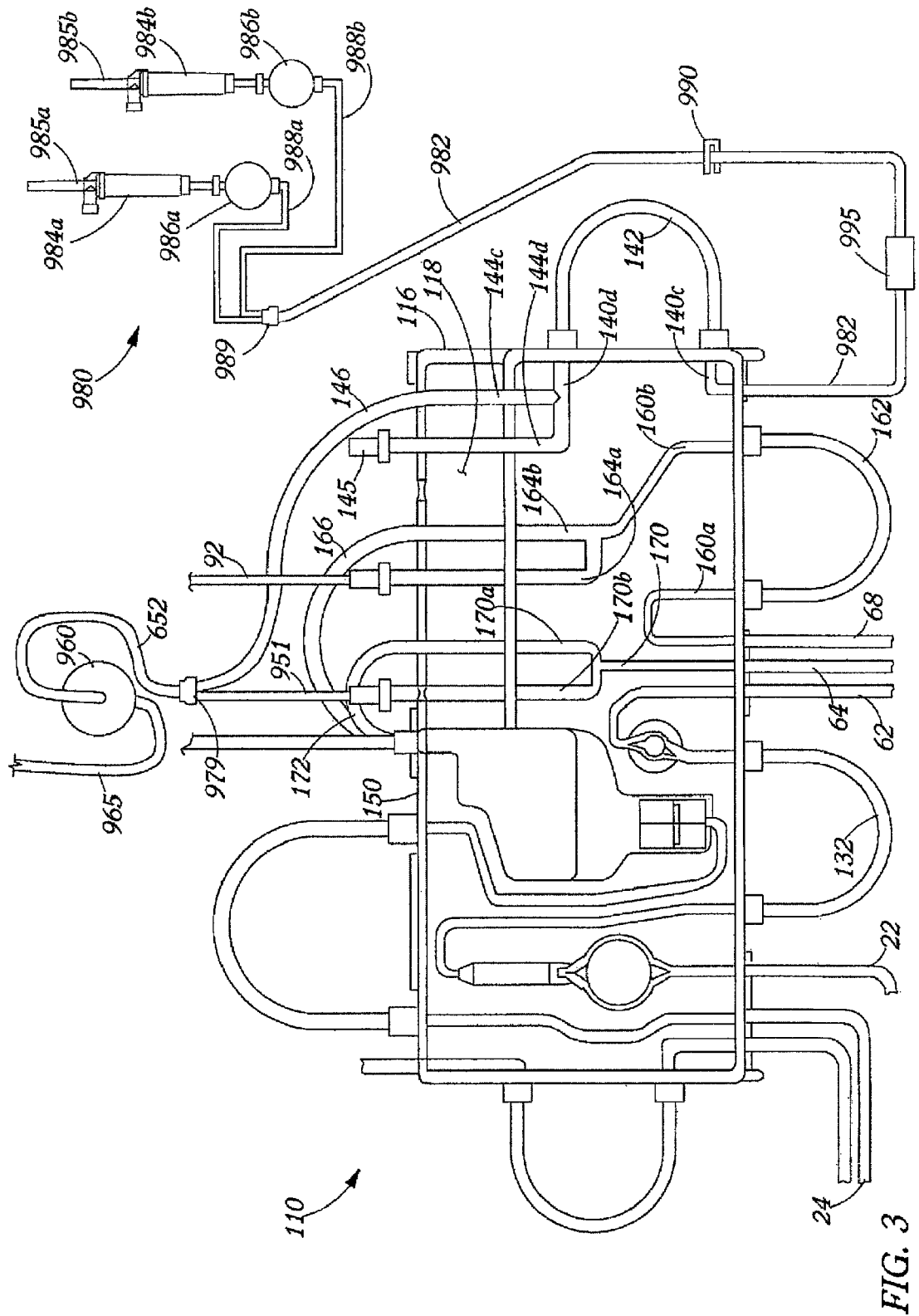
FIG. 3 illustrates a cassette assembly similar to that shown in the set of FIG. 2.
Figure 4:
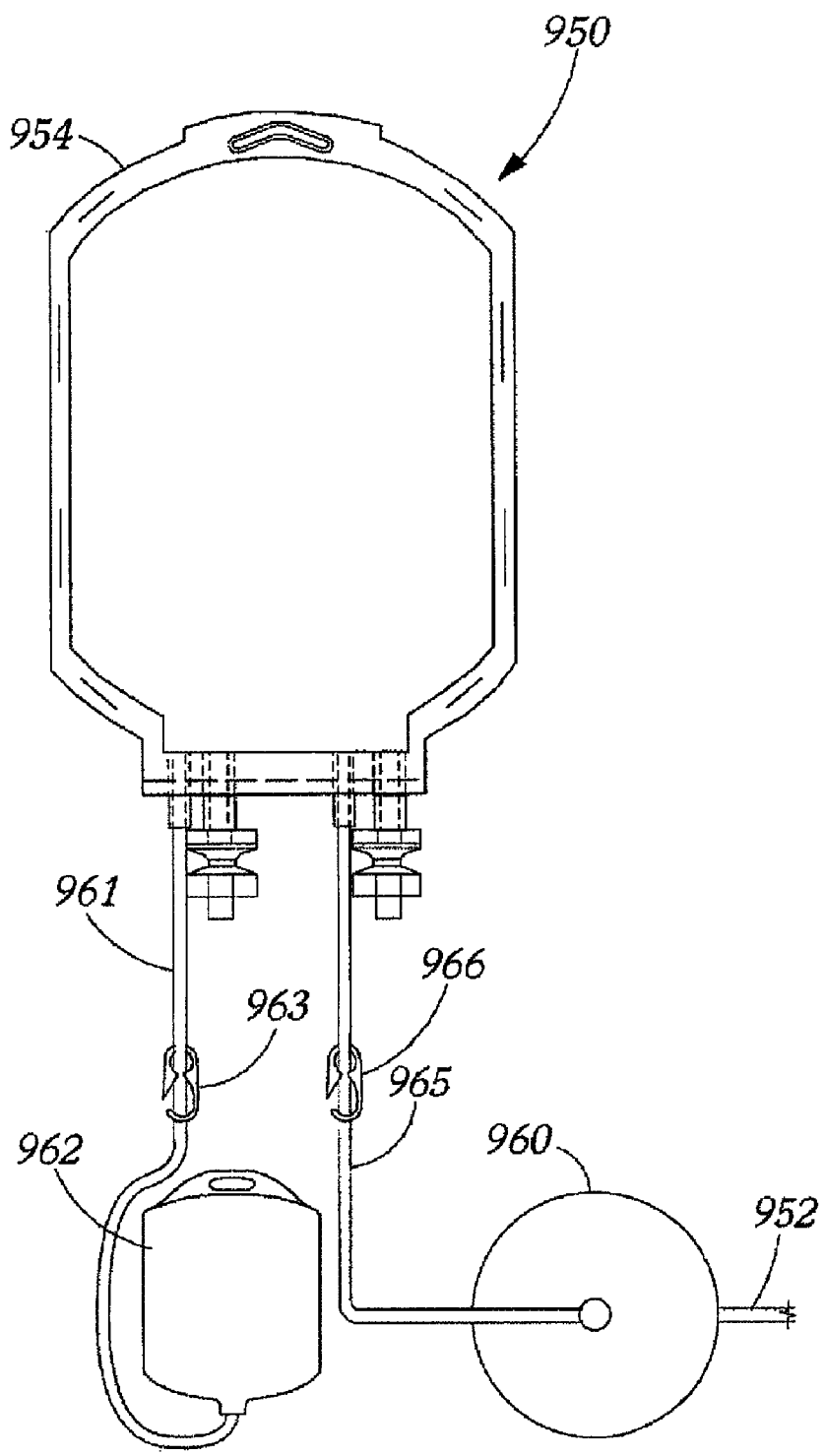
FIG. 4 illustrates a filter and collection bag assembly similar to that shown in the set of FIG. 2.

As illustrated in FIGS. 2, 3 and 4, a preconnected extracorporeal tubing circuit 10 is shown which may include a cassette assembly 110 and a number of tubing/collection assemblies 20, 50, 60, 100, 90, 950 and 980 interconnected therewith. Preferably, a blood removal/return tubing assembly 20 provides a single needle interface between a donor 4 and the remainder of the tubing circuit 10 (although a two-needle set-up may also be used, not shown). At least two lines 22, 24 are preferably provided in assembly 20 (see FIG. 3) for removal of blood from and return of components to the donor. This embodiment includes a cassette assembly 110, which is interconnected between the tubing assembly 20 which connects the donor 4 thereto, and blood inlet/blood component tubing line sub-assembly 60 which provides the interface between cassette assembly 110 and blood processing vessel 352. Three lines 62, 64 and 68 are shown in FIGS. 2 and 3 for transport of blood and components to and from the processing vessel 352. An anticoagulant tubing assembly 50, a plasma collection tubing and bag assembly 90, a red blood cell collection assembly 950, a vent bag tubing line sub-assembly 100, and an additive solution assembly 980 are also interconnected with cassette assembly 110 in this embodiment. As will be appreciated, the extracorporeal tubing circuit 10 and blood processing vessel 352 are preferably pre-interconnected to combinatively yield a closed, pre-sterilized disposable assembly for a single use.

The disclosures of the above-listed patents include numerous further details of an apheresis system for use with the present invention. Such details are not repeated here except generally for certain of those which may relate particularly to red blood cell (hereafter, RBC) collection and/or other RBC processes. Other blood component separation and collection processes are discussed at various points herein where they may be involved in or somewhat related to features of the present disclosure.

For a particular example, emanating from vessel 352 is an RBC outlet tubing line 64 of the blood inlet/blood component tubing assembly 60 which is interconnected with integral RBC passageway 170 of cassette 115 of cassette assembly 110 (see FIGS. 2 and 3). The integral RBC passageway 170 includes first and second spurs 170a and 170b, respectively. The first spur 170a is interconnected with RBC return tubing loop 172 to return separated RBCs to a donor 4. For such purpose, the RBC return tubing loop 172 is preferably interconnected to the top of a blood return reservoir 150 of the cassette assembly 110. The second spur 170b may, as preferred herein, be connected with an RBC collection tubing assembly 950 (see FIGS. 2, 3 and 4, for example) for collecting RBCs during use. RBC collection tubing and bag assembly 950 preferably includes RBC collector tubing line 951 which communicates with spur 170b, a second collector tubing line 952 communicating with line 951, an RBC filtration sub-assembly including an RBC leukoreduction filter 960, an RBC collection reservoir or bag 954, and an air removal bag 962. Bag 954 is connected to the filter 960 by tubing line 965. An optional clamp 966 (see FIG. 4) may be included on line 965. The air removal bag 962 is attached to the RBC collection bag 954 by a tubing line 961 which may have an optional clamp 963, (FIG. 4), attached thereto. The RBC collection tubing line, filter and container sub-assembly 950 is preferably a preconnected part of the disposable assembly 8/10.

Figure 5A:
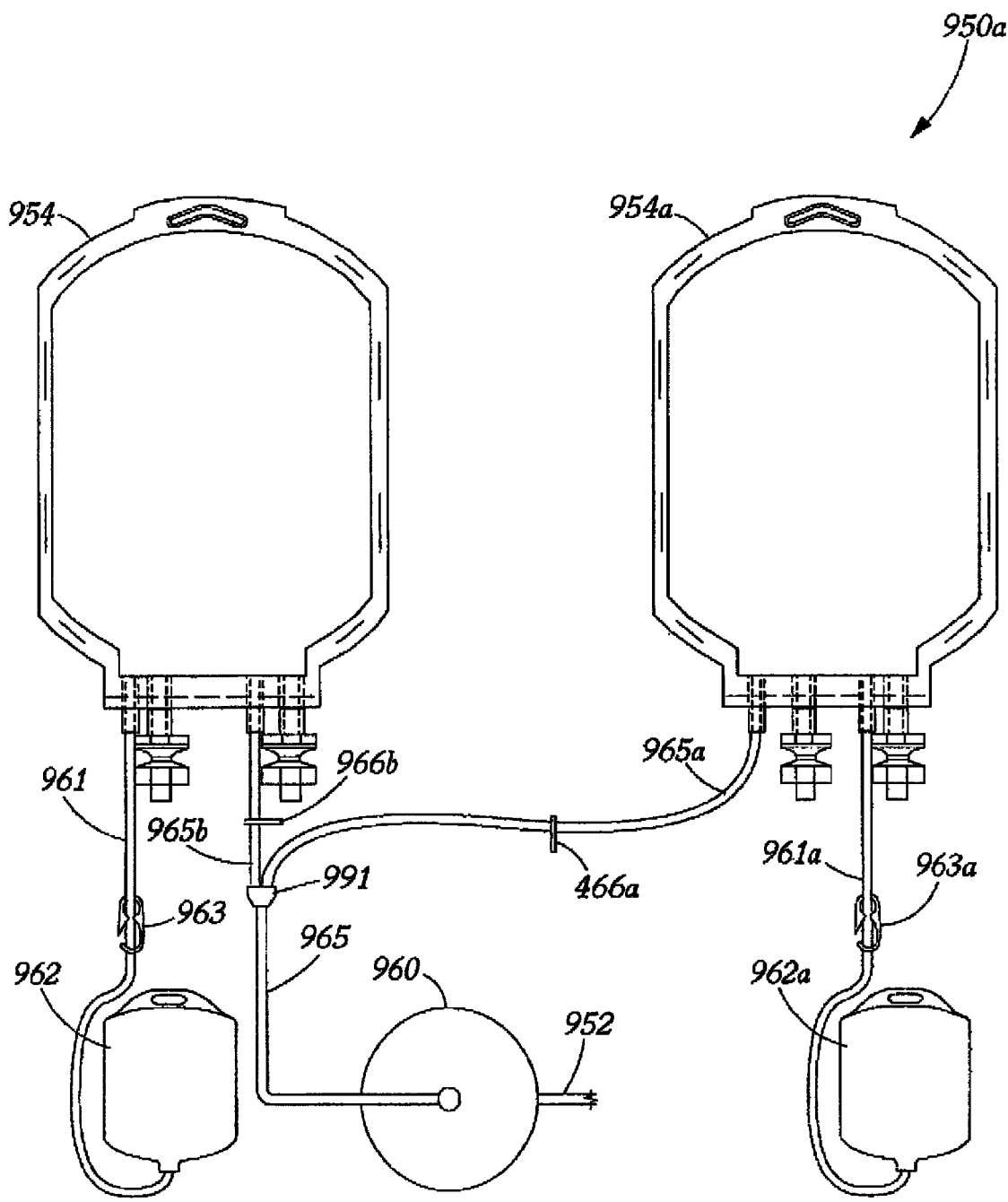
FIGS. 5A and 5B illustrate alternative filter and collection bag assemblies also usable in a tubing and bag set like that shown in FIG. 2.

An alternative tubing set filter and collection bag assembly 950a is shown in FIG. 5A and includes a second collection bag 954a connected via a Y-type of connection 991 to filter 960, via the branch tubing line 965a. A further air bag 962a is preferably connected to the second bag 954a via a tubing line 961a. Slide clamps 966a and 966b are used to direct flow to the desired bag. More details particularly as to the use hereof will be set forth below.

Figure 5B:
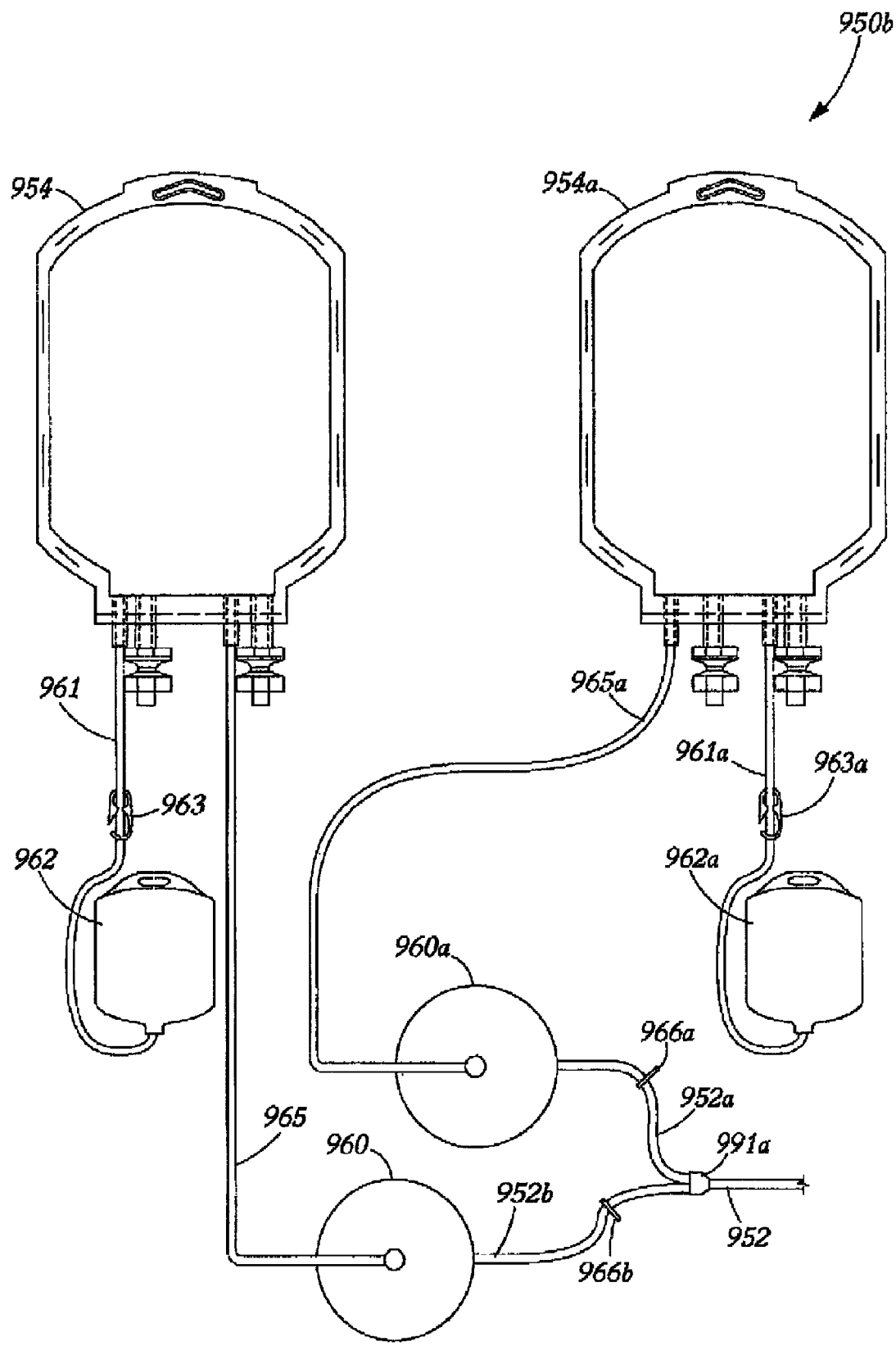

A further alternative embodiment is shown in FIG. 5B, which embodiment is an assembly 950b which also includes a second collection bag 954a with associated componentry (e.g., air bag 962a, etc.), and a second filter 960a, in addition to filter 960 described above which is connected via lines 952a and 965a between bag 954a and incoming line 952. A branch or Y connector 991a allows for split flows between branch 952a and branch 952b which leads to the first filter 960. Also slide clamps 966a and 966b may again be used to direct the flow to the respective filters.

The embodiment shown in FIG. 1 includes a connected pair of additive solution bags 970; however the alternative embodiments of FIGS. 2 and 3 preferably have an additive fluid tubing assembly 980 for attachment to and delivery of additive fluid(s) such as sterile saline solution(s), or additive plasma or additive storage solution, for example, to the collected or collecting product in bag system 950 as described in further detail below. As shown in FIGS. 2 and 3, the additive fluid assembly 980 includes at least an additive fluid inlet tubing line 982 attached to the cassette 110 in fluid communication with an internal additive fluid passageway 140c which is in turn connected to an additive fluid tubing loop 142 which is connected back to the cassette 110 and an internal additive fluid passageway 140d. Two further internal passageways or spurs 144c and 144d and tubing 145 and 146 are also shown in the alternative embodiment of FIGS. 2 and 3. These passageways 140c, 140d and 144c, 144d and tubing loops/tubing 142, 145 and 146 are as shown, preferably similar structurally to the platelet passageways described in various of the above-referenced U.S. Patents, though they may take other forms as well. Indeed, the alternative internal passageway 144d and tubing145 of the embodiment of FIGS. 2 and 3 may as shown, be blocked off to disallow any fluid flow therein or therethrough. Note, although no outlet tubing line is connected thereto in this embodiment, these flow channels could correspond to a platelet or other blood component collection line as understood in the art, and please see an alternative use in conjunction with a platelet collection assembly which will be described relative to FIG. 9, below. Though similar structurally in many ways, when referring to the embodiment of FIGS. 2 and 3, the component elements thereof will be referred to as additive fluid elements as opposed to platelet assembly components. This alternative naming convention will also be used for other component elements which could be referred to in connection with either the platelet assembly or the additive fluid assembly; for example, the platelet or additive fluid inlet pump (described in the art) will hereafter be referred to as an additive solution pump. Note, one further distinction is the connection of tubing connector 146 to tubing lines 951 and 952 via connector 979.

The additive fluid assembly 980 further preferably includes one or more (as shown) spike assemblies 984a, 984b with respective spikes 985a, 984b and associated sterile barrier devices 986a, 986b and tubing connection lines 988a, 988b which may be connected to tubing line 982 via a Y-connector 989 as shown. Note, it may be that only one of one or more of the above devices may be necessary; e.g., perhaps only one sterile barrier device may be used even with more than one bag of solution. One or more slide clamp(s) 990 and/or a level sensing or fluid detection apparatus 995 may also be included.

The cassette assembly 110 further includes a pump-engaging, additive fluid inlet tubing loop 142 interconnecting the first respective integral additive fluid passageway 140c and a second integral additive fluid passageway 140d. The second integral or additive fluid passageway 140d includes first and second spurs 144c, 144d, respectively. The second spur 144c of the second additive fluid passageway 140d (FIGS. 2 and 3) is interconnected with additive fluid tubing 146 to deliver additive fluid through the RBC outlet line 952 for ultimate delivery to the filter 960 and then to the bag 954. The cassette member 115 also includes an integral frame corner 116 defining a window 118 therethrough. The frame corner 116 includes access openings in window 118 for receiving and orienting the tubing segments including, for example, connector 145 and additive solution tubing 146 in predetermined spaced relationships within window 118 for ultimate engagement with a valve/clamp member on apheresis device 6. Such a valve/clamp will, when activated, control flow through loop 146, e.g.

In an intervening portion of the cassette 115, a plasma tubing 68 of blood inlet/blood component tubing assembly 60 (see FIGS. 2 and 3) interconnects with a first integral plasma passageway 160a (see FIG. 3) of cassette assembly 110 (note, this is preferably a plasma collection sub-system; however, other components such as platelets could alternatively be collected here or with a similar arrangement). Cassette assembly 110 further includes a pump-engaging, plasma tubing loop 162 interconnecting the first integral plasma passageway 160a and a second integral plasma passageway 160b. The second integral plasma passageway 160b includes first and second spurs 164a and 164b. The first spur 164a is interconnected to the plasma collection tubing assembly 90 via tubing line 92. The plasma collection tubing assembly 90 may be employed to collect plasma during use and includes plasma collector tubing 92 and plasma collection bag 94. A slide clamp 96 (see FIG. 2) may be provided on plasma collector tubing 92. The second spur 164b of the second integral plasma passage-way 160b is interconnected to a plasma return tubing loop 166 to return plasma to donor/patient 4. For such purpose, the plasma return tubing loop 166 is interconnected to the top of the blood return reservoir 150 of the cassette assembly 110. As is understood, one or more types of uncollected blood components, e.g., plasma and/or platelets, collectively referred to as return blood components, will cyclically accumulate in and be removed from reservoir 150 during use. Here also, valve/clamp access is made through the frame 116 within window 118 of cassette assembly 110 to maintain the plasma collector tubing 92 and plasma return tubing loop 166 in a predetermined spaced relationship within window 118 for flow control therethrough.

Most portions of the tubing assemblies 20, 50, 60, 90, 100, 950, 950a, 950b and/or 980 and cassette assembly 110 are preferably made from plastic components including, for example, polyvinyl chloride (PVC) tubing lines, that may permit visual observation and monitoring of blood/blood components therewithin during use. It should be noted that thin-walled PVC tubing may be employed for approved, sterile docking (i.e., the direct connection of two pieces of tubing line) for the RBC collector tubing lines 952 and 965, as may be desired and/or for an RBC storage solution spike assembly 980, inter alia. In keeping with one aspect of the invention, all tubing lines are preconnected before sterilization of the total disposable assembly to assure that maximum sterility of the system is maintained. Note, a highly desirable advantage to preconnection of all of the elements of the tubing circuit including the filter and collection bag sub-assembly 950 involves the complete pre-assembly and then sterilization hereof after pre-assembly such that no sterile docking is later necessary (spike addition of storage solution excepted). Thus, the costs and risks of sterile docking are eliminated. Alternatively, thicker-walled PVC tubing may be employed for approved, sterile docking RBC collector tubing lines 952 and/or 965, inter alia.

As mentioned, a cassette assembly 110 in the embodiment of FIG. 3, may be mounted upon and operatively interface with the pump/valve/sensor assembly 1000 of a blood component separation device 6 during use. Further details of an apheresis system set-up including the loading and interaction of a disposable assembly 8/10 with a blood component separation device 6, may be found in the above-listed patents, inter alia, and are not exhaustively repeated here.

Operation of Extracorporeal Tubing Circuit and Blood Component Separation Device Priming and various other operations of the apheresis process are preferably carried out as set forth in the above-listed patents, inter alia. However, certain basic features are also described generally here with particular reference to the schematic diagrams of FIGS. 6, 7, and 8, as well as with continuing reference to FIGS. 1-5. It is understood the filtration and RBC collection will also generally be the same for the alternative embodiments of FIGS. 10, 11 and 12, except for the additive solution assembly and the particular processing vessel used.

Figure 6:
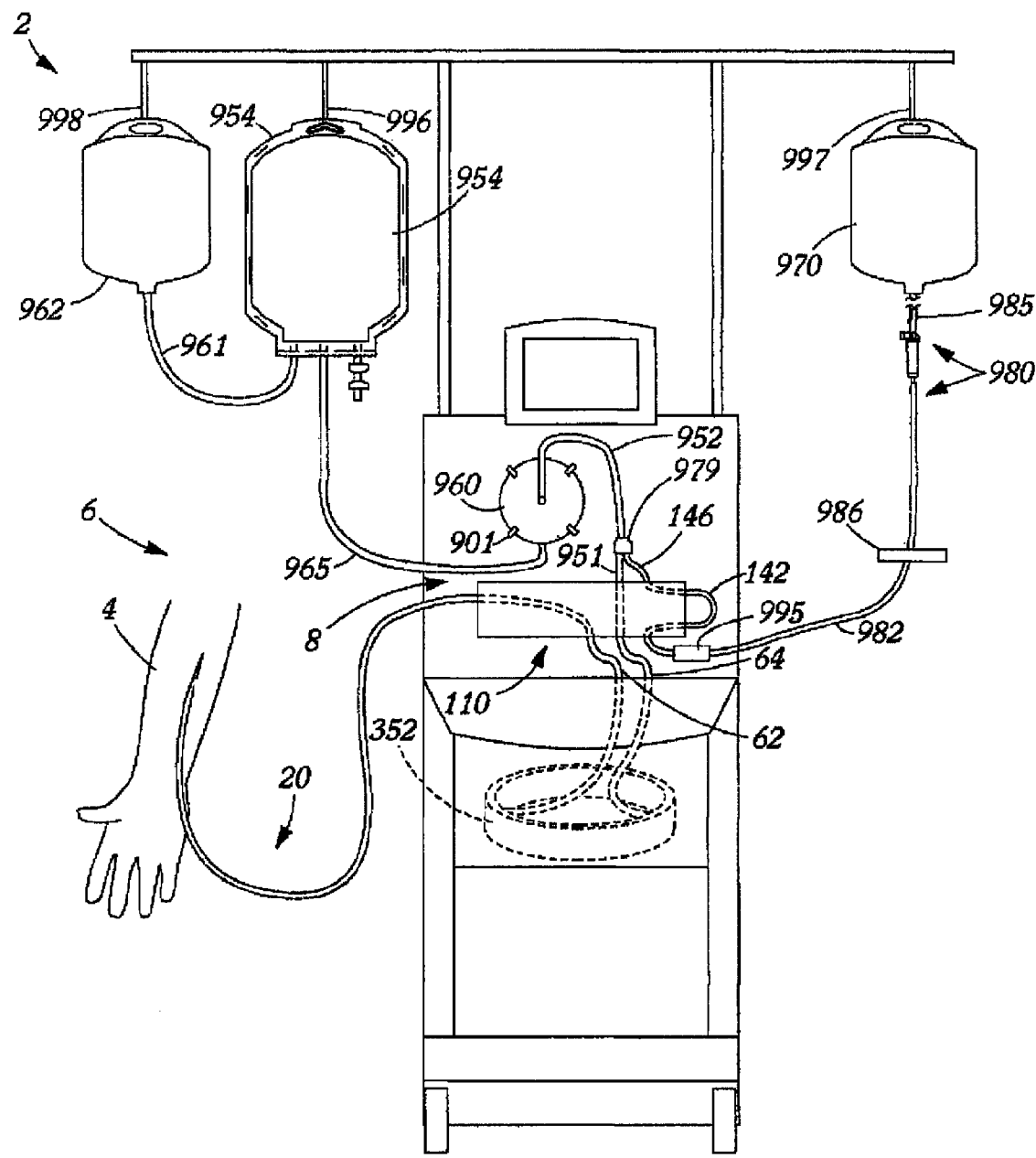
FIG. 6 is a schematic view of an apheresis system according to the present invention.

For example, during a blood removal submode, whole blood will be passed from a donor 4 into tubing line 22 of blood removal/return tubing assembly 20 and is then transferred to blood component separation device 6 (see generally FIG. 6). At device 6, the blood is flowed, preferably pumped via loop 132 (see FIG. 3), to the processing vessel 352 (schematically shown in dashed lines in FIG. 6) via the cassette assembly 110 and line 62 of the blood inlet/blood component tubing assembly 60 (FIGS. 2 and 3). Separation processing then occurs preferably on a substantially continuous basis in vessel 352; i.e., blood substantially continuously flows therein, is continuously separated and continuously flows as separated components therefrom. After separation processing in vessel 352 (though separation is continuously occurring), uncollected blood components are transferred from the processing vessel 352 to and through cassette assembly 110, into and may then accumulate in reservoir 150 (FIGS. 2 and 3) of cassette 110 up to a predetermined level at which the blood component separation device 6, in a single needle operation, may (though in a continuous system, need not) pause the blood removal submode and initiate a blood return submode wherein these uncollected and/or treated components may be returned to the donor 4. As such, these accumulated components may be transferred into the blood return tubing line 24 of blood removal/return tubing assembly 20 and back into the donor 4. During the single needle blood return mode, when the accumulated return blood components in reservoir 150 are removed down to a predetermined level, blood component separation device 6 will then automatically end the blood return submode. This preferably will also automatically serve to reinitiate or continue the blood removal submode. The cycle between blood removal and blood return submodes will then continue until a predetermined amount of RBCs or other collected blood components have been harvested. In an alternative dual needle scheme, as is known in the art, blood may be continually removed from and blood components continually returned to a donor 4. Note, the detailed mechanisms for such operations, including controlling the pumps, for example, are not shown or described in detail herein, particularly not in the schematic views of FIGS. 6 and 7.

Note also that certain components may be collected simultaneously or consecutively one after the other. In one example, platelets may be collected prior to collection of RBCs while plasma may be collected concurrently with either. A particular example of this will be described relative to the embodiments shown in FIGS. 9-12, below. In the primary example shown in FIGS. 1-3 and 6, 7 and 8, only two components are shown being collected, RBCs in the RBC sub-assembly 950 and plasma (or platelets) in the other collection assembly 90. When a sufficient quantity of one or the other is collected, further separated portions of such a component are preferably returned to the donor with any other uncollected components, until a sufficient quantity of all components are collected. It is further understood that only RBCs can be collected with all other components including plasma being returned to the donor.

With specific reference to FIGS. 2 and 3, in normal operation, whole blood will pass from the donor 4 through the needle and blood removal tubing assembly 20, cassette assembly 110 and blood inlet tubing line 62 to processing vessel 352. The whole blood will then be separated in vessel 352. Although not shown, a platelet (or plasma) stream may be separated herein and be either collected in a collector assembly (not shown, but see FIGS. 10, 11,12. and 13), or diverted to reservoir 150 for ultimate return to the donor. Similarly, separated plasma (or alternatively, platelets) may also be separated in vessel 352 and either be flowed through cassette 110 (via line 68 and loop 162) for collection in the container 94 of plasma (or platelet) tubing assembly 90 and line 92 or diverted to reservoir 150. Further, red blood cells (including potentially some white blood cells) may be separated in and passed, preferably pushed from vessel 352 through RBC outlet tubing line 64, through cassette assembly 110 and, in return mode, into reservoir 150. In a preferred alternative, during an RBC collection procedure described hereinbelow, separated RBCs will be delivered to RBC collector tubing, bag and filter assembly 950 through tubing lines 951 and 952 for collection. The RBC collection protocol may also, and preferably does as described herein, include an RBC filtration process using the preconnected leukoreduction filter 960 in line with and prior to RBC collection bag 954. This procedure will be described further below.

Further details of apheresis processing for the separation of blood into its components may be found in the above-listed patents inter alia and are not substantially repeated here. It may be noted, however, that although alternative separation mechanisms exist, centrifugation is the preferred separation process which is preferably effected by a channel assembly 200 rotated, for example, by a centrifuge rotor assembly 568 in a device 6 (see FIG. 1). Channel assembly 200 would then preferably include a channel housing 204 which would receive a disposable blood processing vessel 352 of a tubing circuit 10 (see FIGS. 1 and 2).

Apheresis Protocol

One preferred protocol, which may be followed for performing an apheresis procedure relative to a donor 4 utilizing the described system 2, will now be summarized. Initially, an operator loads the disposable plastic assembly 8 in and/or onto the blood component separation device 6. According hereto, the operator hangs the various bags (e.g., collection bag 954 (and 94, if used); see FIG. 6, described further below) on the respective hooks (see hook 996 of FIG. 6, e.g.) of the blood component separation device 6. If one is used, the operator then also loads the cassette assembly 110 on the machine 6 and/or the blood processing vessel 352 within the channel housing 204 as mounted on the centrifuge rotor assembly 568 in the machine 6.

With the extracorporeal tubing circuit 10 and the blood processing vessel 352 loaded in the described manner, the donor 4 may then be fluidly interconnected with the extracorporeal tubing circuit 10 by inserting an access needle of the needle/tubing assembly 20 into the donor 4 (see, e.g., FIG. 6). In addition, the anticoagulant tubing assembly 50 (see FIG. 2) is primed and the blood removal/return tubing assembly 20 is primed preferably with blood from the donor 4 as described in one or more of the above-listed patents, inter alia. The blood processing vessel 352 is also primed for the apheresis procedure, preferably also according to processes such as those described in the same above-listed patents. In one embodiment, a blood prime may be used in that blood will be the first liquid introduced into the blood processing vessel 352. During the priming procedure, as well as throughout the remainder of the apheresis procedure, blood may be continuously flowed into the vessel 352, blood component types are preferably continuously being separated from each other and one or more of these is also preferably continuously removed from the blood processing vessel 352, on a blood component type basis. Preferably, at all times during the apheresis procedure, from priming onward, a flow of blood is substantially continuously provided to the blood processing vessel 352 and at least one type of separated component is continually removed.

Although separation and collection of various components may be performed, RBCs are the component of the most interest in the current invention, and thus the separation and collection protocol will continue with a description of the collection and filtration hereof. Again, it is understood that RBCs may be the only component collected with all other components being returned to the donor.

The preferred blood apheresis system 2 provides for contemporaneous separation of a plurality of blood components during blood processing, including at least the separation of red blood cells (RBCs) and plasma, but optionally may provide for the separation and collection of platelets (not directly shown here), inter alia. In turn, such separated blood components may be selectively collected in corresponding storage reservoirs (FIGS. 10-12) or immediately or after a minor delay returned to the donor 4 during respective blood return submodes (or substantially constantly in a two-needle setup). In this regard, and in one approach where more than one blood component is to be collected, such as both plasma (and/or platelets) and RBCs, blood apheresis system 2 may be used to collect plasma (and/or if desired separated platelets), during a time period(s) separate from the collection of red blood cells. These components may also be collected simultaneously. Note, if other components are collected prior to RBCs, then RBCs separated during any such other component phase may be diverted back to the donor and not filtered. Preferably, only collected RBCs will be filtered in the current embodiment (though therapeutic filtration for a particular donor/patient may also be performed).

In any event, the RBC collection procedure is preferably controlled via control signals provided by blood collection device 6. Such an RBC collection procedure may include a setup phase and a collection phase. During such a setup phase, the blood apheresis system 2 may (as in the preferred embodiment) be adjusted automatically to establish a predetermined hematocrit in those portions of the blood processing vessel 352 and extracorporeal tubing circuit 10 through which separated RBCs will pass for collection during the RBC collection phase. A desirable resulting hematocrit for RBC collection may be between about 70 and about 90 or even up to 95+, and may preferably be established at about 80. The term high hematocrit is intended to refer to such a range and refers to those separated RBCs leaving the separation vessel 352. Dilution with storage solution to a different (generally lower) collected hematocrit will follow. Additionally, blood component device 6 may, during the set-up phase, divert the flow of separated RBCs flowing through RBC tubing line 64 through return tubing loop 172 and into blood return reservoir 150 for return to the donor 4 until the desired hematocrit is established in the separation system. Then, blood component separation device 6 may also selectively control the diversion of the plasma and platelets (if separated here) into reservoir 150 for return to the donor 4.

In order to establish the desired packing factor and/or hematocrit for the separated RBCs, the operating speed of centrifuge rotor assembly 568 (see FIG. 1) may be selectively established via control signals from blood component separation device 6, and the blood inlet flow rate to vessel 352 may be selectively controlled by blood component separation device 6 controlling the speeds of the respective pump assemblies (not shown or described in detail here). More particularly, increasing the rpms of centrifuge rotor assembly 568 and/or decreasing the inlet flow rate will tend to increase the packing factor and/or hematocrit, while decreasing the rpms and/or increasing the flow rate will tend to decrease the packing factor and/or hematocrit. As can be appreciated, the blood inlet flow rate to vessel 352 may effectively be limited by the desired packing factor or hematocrit.

To establish a desired anticoagulant (AC) ratio, blood component separation device 6 provides appropriate control signals to the anticoagulant pump so as to introduce anticoagulant into the blood inlet flow at a predetermined rate. Relatedly, it should be noted that the inlet flow rate of anticoagulated blood to blood processing vessel 352 may be limited by a predetermined, maximum acceptable anticoagulant infusion rate (ACIR) to the donor 4. As will be appreciated by those skilled in the art, the predetermined ACIR may be established on a donor-specific basis (e.g. to account for the particular total blood volume of the donor 4). To establish the desired total uncollected plasma flow rate out of blood processing vessel 352, blood collection device 6 provides appropriate control signals to the plasma (and platelet) pump assembly(ies). This may also serve to increase the hematocrit in the separated RBCs.

In one preferred embodiment, the desired high hematocrit for the separated RBCs will be between about or approximately 75 and about 85 and will preferably be about or approximately 80; although, again higher hematocrits may be available as well. It is less preferred to have the hematocrit as low as approximately 40 or as high as approximately 95. Then, where a preferred centrifuge rotor assembly 568 may present a defined rotor diameter of about 10 inches, and where a blood processing vessel 352 is utilized, as described hereinabove, it has been determined that in one preferred embodiment channel housing 204 can be typically driven at a rotational velocity of about 3000 rpms to achieve the desired RBC hematocrit during the setup and red blood cell collection phases. Correspondingly, the blood inlet flow rate provided by pumping through loop 132 to vessel 352 may preferably be established at below about 65 ml/min. The desired hematocrit can be reliably stabilized by passing about two whole blood volumes of vessel 352 through vessel 352 before the RBC collection phase is initiated.

To initiate the RBC collection phase, blood component separation device 6 provides an appropriate control signal to the RBC divert valve assembly (not shown) so as to direct the continuous outflow of the separated high hematocrit RBCs removed from blood processing vessel 352 via line 64 into the RBC collection system 950 through tubing lines 951 and 952, and filter 960 into collection container 954 via line 965.

As may be appreciated, in the preferred embodiment, the separated RBCs are preferably not pumped out of vessel 352 for collection, but instead are flowed out vessel 352 and through extracorporeal tubing circuit 10 by the pressure of the blood inlet flow to vessel 352. The inlet blood is pumped into vessel 352 via loop 132 of cassette 110. The separated RBCs are pushed or pressed but preferably not pumped out of the vessel 352. Trauma to the collected RBCs would thereby be minimized.

During the RBC collection phase, the inlet flow into vessel 352 will likely be limited by the above-noted maximum acceptable ACIR to the donor 4. The desired inlet flow rate may also be limited by that necessary to maintain the desired packing factor and/or hematocrit, as also discussed. In this regard, it will be appreciated that relative to the setup phase, the inlet flow rate may be adjusted slightly upwards during the RBC collection phase since not all anticoagulant is being returned to the donor 4. That is, a small portion of the AC may remain with the small amount of plasma that is collected with the high hematocrit RBCs in RBC reservoir 954.

According to the present invention, the relatively high hematocrit (high-crit) RBCs optionally may be diluted and then filtered as soon as the RBCs are separated or very soon after having been separated within vessel 352. Alternatively, the RBCs may be filtered without dilution in a high-crit state. Preferably, the phrase high-crit refers to the state of the separated RBCs as they emerge from the separation vessel 352. In the substantially continuous centrifugal separation process as described here, a freshly separated stream of RBCs is substantially continually flowing out of the vessel 352, first through tubing line 64, to and through cassette assembly 110 and then through lines 951 and 952 (where they optionally may be joined by diluting storage solution) to the filter 960 and then through line 965 to bag 954 (see FIG. 6). Preferably, these freshly separated RBCs will be continuously flowing from vessel 352 through filter 960 and then into collection bag 954 (or also into bag 954a, see FIGS. 5A and 5B). Thus, in the described embodiment, white cell/leukocyte filtration will have begun and is continued simultaneously with or during the overall continuous separation process, prior to collection. More description of this will be set forth in further detail below.

Note, the phrase freshly-separated is intended to describe the newly-separated blood components in and as they emerge from the mechanical separation system such as device 6 and processing vessel 352. It also includes the state of these same separated components for a reasonable length of time after removal from the mechanical separation device such as from vessel 352. As a general matter, freshly-separated thus relates to the state of these components particularly as they exist at least during the length of the overall separation procedure, but also preferably extends to reasonable periods there beyond. Thus, for example, a first reasonable period may include the entire apheresis procedure which may last up to (and perhaps exceed) two (2) or more hours during which filtration may be substantially continuously performed. Two further terms used herein have similar distinctions, namely, "recently removed" and "soon after." Recently removed is referred to herein primarily relative to that blood taken from the donor which may be immediately taken and processed in a mechanical separation system, or which may have been taken and held subject to a reasonable non-long-term-storage type of delay prior to separation processing in a device such as device 6. Similarly, "soon after" is used in like manners relative to both of these circumstances as well, as, for example, when separated blood components may be removed from the separation vessel, e.g. soon after separation (whether in continuous or batch mode).

In any event, from the standpoint of the donor 4 and machine 6, following the separation, filtration and collection processes of the desired quantity of red blood cells, blood separation device 6 may then provide a control signal to the RBC divert assembly so as to divert any further RBC flow back to the donor 4 via loop 172, reservoir 150 and return line 24. Additionally, if further blood processing, by apheresis centrifugation here, is not desired, rinseback procedures may be completed. Additionally, once the minimum desired RBCs have been diverted into filtration/collection assembly 950 and after filtration completion, the red blood cell collection reservoir 954 (and/or the entire sub-assembly 950) may then be disconnected from the extracorporeal tubing circuit 10. Filter 960 may also be removed herewith or separately or remain attached and disposed of with the cassette 110 and other remaining bags or tubes. However, according to the present invention, a storage solution will be, perhaps during and/or after filtration of the RBCs, added to the RBC flow in tubing line 952 to the filter 960 ultimately to the red blood cell reservoir or bag 954. Preferably, a spike connection to one or more storage solution bag(s) 970 (see FIGS. 1 and 6) through a spike 985 is used. This process will also be described further below. Such storage solutions or additive solutions may advantageously facilitate storage of the RBCs for up to about forty-two days at a temperature of about 1-6 degrees C. In this regard, acceptable storage solutions include a storage solution generically referred to in the United States as Additive Solution 3 (AS-3), available from Medsep Corp. located in Covina, Calif.; and/or a storage solution generically referred to in Europe as SAG-M, available from MacoPharma located in Tourcoing, France. It is also possible to use saline before, after or during the in the filtering process described below which, prior to storage, could be replaced with the desired storage solution. Alternatively saline could be used to flow through the filter 960 to the cassette assembly 110 as more particularly described with reference to FIG. 13 below.

The storage additive solution may be and preferably is contained in a discrete storage solution bag 970 that can be pre-connected, or is separate and may selectively be later interconnected to the tubing circuit 10 via line 982, preferably through a spike connection 985. In an alternative embodiment, such selective interconnection may be provided via sterile-docking to tubing line 982 as an example (process not shown) utilizing a sterile connecting device (not shown). By way of example, one such sterile connecting device to interconnect a tubing line 982 to such a storage solution container 970, is that offered under the trade name "TSCD" or "SCD™ 312" by Terumo Medical Corporation located in Somerset, N.J. In the alternative above, the selective interconnection may be established utilizing a sterile barrier filter/spike assembly 980. The use of such a sterile barrier filter/spike assembly 980 facilitates the maintenance of a closed system, thereby effectively avoiding bacterial contamination. By way of example, the mechanical, sterile barrier filter 986 (FIG. 6) or 986a or 986b in such an assembly 980 may include a porous membrane having 0.2 micron pores. Pumping via a tubing loop 142 may then provide for selectively flowing solution through tubing line 982 and connecting tubing line 146 for introduction of the storage solution into the RBC line 952 and filter system 950.

In order to ensure the maintenance of RBC quality, the collection RBC bag 954, and the storage solution and the anticoagulant used during blood processing should be compatible. For example, the collection RBC reservoir 954 may be a standard PVC DEHP reservoir (i.e. polyvinyl chloride-diethylhexylphthallate) such as those offered by the Medsep Corporation. Alternatively, other PVC reservoirs may be employed. Such a reservoir may utilize a plasticizer offered under the trade name "CITRIFLEX-B6" by Moreflex located in Commerce, Calif. Further, the anticoagulant utilized in connection with the above-described red blood cell collection procedures may be an acid citrate dextrose-formula A (ACD-A).

Nevertheless, according to an embodiment of the present invention as introduced above, the storage solution may be flowed after and/or added to the flow of separated red blood cells flowing in lines 951 and 952, and flow therewith to and through the filter 960 which will preferably remove a satisfactory quantity of white blood cells from the separated red blood cells. More particularly leukoreduction filtering is desired to establish a white blood cell count of $<5\times10^6$ white blood cells/unit (e.g. about 250 ml.) to reduce any likelihood of febrile non-hemolytic transfusion reactions. Moreover, such filtering will more desirably achieve a white blood cell count of $<1\times10^6$ white blood cells/unit to reduce any risk of HLA (i.e. human leukocyte A) sensitization and/or other serious side reactions. Studies have also shown positive effects for pre-storage leukocyte reduction in improving the functional quality of erythrocytes during storage and in decreasing the occurrence of alloimmunization in patients receiving multiple transfusions, as well as being favorable in metabolism reactions such as intra-erythrocyte ATP and/or extracellular potassium levels declining more slowly in filtered products. Perhaps more important is the reduction of transfusion transmitted disease, especially cytomegalovirus (CMV) and/or HIV, inter alia.

Figure 7:
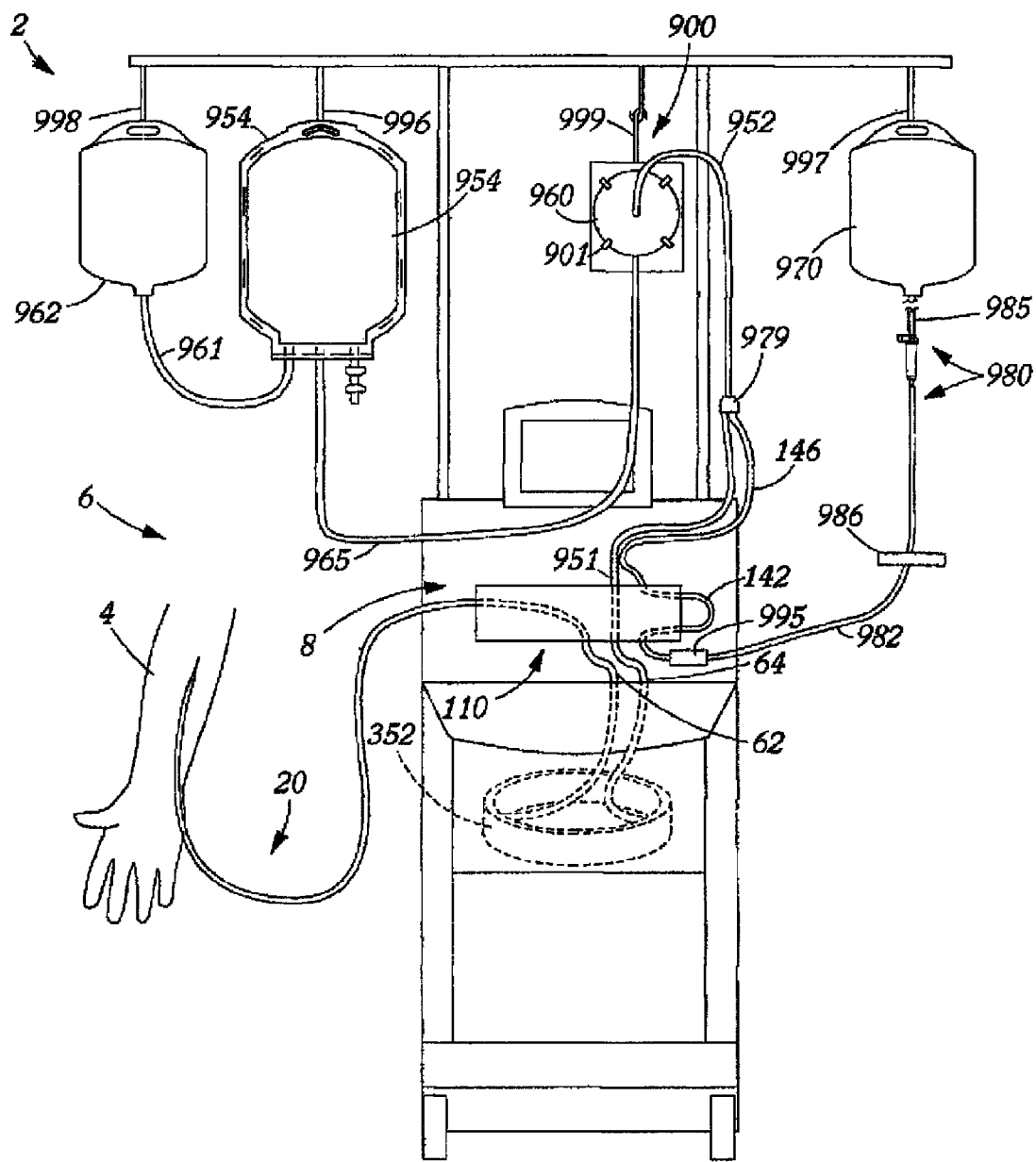
FIG. 7 is a schematic view of an alternative apheresis system also according to the present invention.
Figure 8:
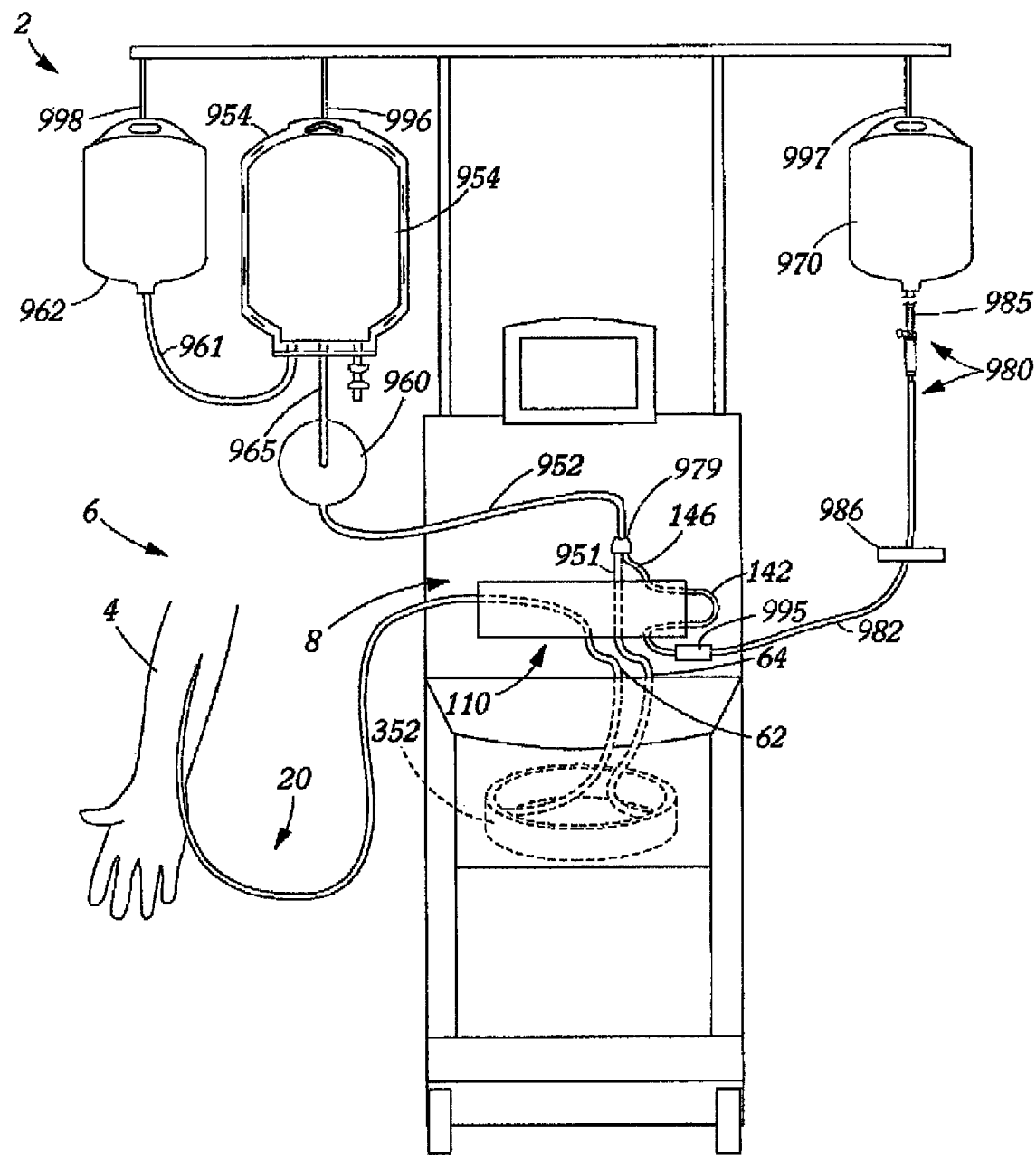
FIG. 8 is a schematic view of an alternative apheresis system according to the present invention.

Accordingly, the red blood cell collection container 954 receives, in one embodiment, RBCs and additive solution from the red cell filter 960 such that high hematocrit (preferably Hct between 70 and 90 and/or approximately equal to 80), freshly separated red blood cells alone or together with additive solution are preferably pushed through filter 960 and into the ultimate RBC collection bag 954. Such pushed filtration is shown in FIGS. 6, 7 and 8, as will be described further below. The red cell filter 960 and collection bag sub-assembly 950 is preferably preconnected to the tubing circuit 8 as part of the disposable assembly 10 (to avoid the costs and risks of sterile docking) as shown in FIGS. 1, 2 and 3 in accordance with the teachings of this invention, or may be added to the previously existing disposable systems to form a post-manufacturing-connectable disposable assembly using special new kits or commercially available filter/bag kits such as those available under the trade names "r\LS" manufactured by HemaSure, Inc. located in Marlborough, Mass., or "Sepacell" from Asahi Corp and/or Baxter, Inc. and/or "RC 100", "RC50" and "BPF4", etc., from Pall Corp., located in Glencove, N.Y., inter alia. In either event, the red cell filter/bag sub-assembly is preferably connected (pre- or post-) to the tubing circuit 8 through a tubing line 951 and/or 952 as shown.

Referring now primarily to FIGS. 2, 3 and 4, the procedure for the filtration of RBCs freshly separated and collected from the apheresis process is as follows. These freshly separated RBCs are either in an undiluted, high-hematocrit state (Hct approximately 80) during the preferred filtration process, and followed by additive solution or storage solution, or are filtered in a mixed state with additive solution added to the RBC flow in line 952 at the connection 979. Moreover, storage solution may be flowed through the filter 960 prior to any RBCs (this may enhance the filtration efficacy) and, as noted above, may optionally be flowed through the filter after leukoreduction of the RBCs to be added to the collected RBCs in bag 954. In the preferred embodiment, no matter when the additive or storage solution initially flows through the filter, it is preferable to run a sufficient amount of solution through the filter 960 after RBC filtration to attempt to displace any RBCs remaining in the volume of the filter 960 for collection.

Either simultaneously with the preferred substantially continuous separation and collection process (i.e., as soon as high hematocrit (high-crit) RBCs are separated from other components and pushed out of vessel 352 to cassette 110 and not diverted back to the donor), or soon after a desired minimum quantity of other blood components have been collected, if desired, the RBC collection/filtration system 950 is activated to filter the RBCs. This collection process is activated by switching the clamp/valve of device 6 to stop diversion flow through loop 172 and allow flow through line 951 to line 952 and filter 960.

In either case; simultaneously with the continuous collection in bag 954 from the separation vessel 352, or soon after completion of any other non-RBC collection process(es), the RBCs are flowed preferably by intrinsic pressure pushing (non-active pumping) through filter 960. As such, collection bag 954 may be hung at a level above both the separation vessel 352 and the filter 960 (see FIGS. 4-7) so that the continuously flowing RBCs are allowed to move upwardly from vessel 352 through the filter 960 and into the collection bag 954. One embodiment of this is shown in FIG. 6, where the collection bag 954 is hung from a hook 996 of the machine 6 in known fashion. Tubing line 965 depends downwardly therefrom and is shown as connected to the filter 960, out of the top of which extends the next tubing line 952 which ultimately connects downwardly to the cassette 110 via line 951.

Any air from bag 954, or air caught between the incoming RBCs and bag 954 is ultimately removed to air removal bag 962 through tubing line connection 961. The air is evacuated to air removal bag 963 prior to the flow of the incoming RBCs or is evacuated by the flow of the incoming RBCs. It is also understood that air can also be vented prior to even the separation process by initially running the return pump, (not shown) of the apheresis system. It is also understood that removal of air may also be achieved by other known (though less desirable here) methods, including, for example, hydrophobic vents and/or by-pass lines. It is desirable to perform the filtering of the RBCs according to the present invention directly on the machine 6 during the apheresis separation process and without pre-cooling or pre-storing the RBCs. In such a case, these procedures are thus performed without the previously conventional steps of intermediate separation/collection and cooling and storing overnight at 4 degrees Centigrade.

Then, either after completion of or during and/or even before the filtration in either of these embodiments, namely, the simultaneous collection and filtering, or in the filtering and collection soon after any other component collection processes, storage solution is flowed to and through the filter and/or added to the RBCs. Again, this may be performed either before and/or during and/or after completion of the filtration of the otherwise high hematocrit RBCs through filter 960, although it is preferred that an amount of additional additive or storage solution displace the volume of the filter to recover any residual RBCs therefrom. In particular, a storage solution bag 970 has been connected (by pre-connection or by spike or sterile welding) as depicted in FIGS. 1, 6, 7 and 8, the clamp 990 is opened (if any such optional flow-stopping member is used; see FIGS. 2 and 3) to allow the introduction of the storage solution into tubing line 982 and pumped via tubing loop 142 through loop 146 and into tubing line 952 via connector 979. The storage solution thus will be pumped from bag 970 through filter 960 and into collection bag 954. If pumped during collection, the solution may be metered into and mix with and dilute the high-crit RBCs in line 952 prior to filtration. The rate of mixing can be controlled by pumping via loop 142. However, the storage solution may be pumped through the filter 960 also before and/or after all of the undiluted RBCs have been filtered therethrough to assist in the filtration and/or to chase the RBCs and move RBC volume caught in the filter out of the filter to the collection bag 954. Such a storage solution chase may be used also after the metering of storage solution into a pre-filtration RBC flow (as described above) as well. Again, all of the steps in operating the RBC filtration system 950 may be performed during the overall apheresis component separation procedure and thus need not be subjected to a cooled, time-delayed environment, such as the 4 degrees Centigrade overnight procedures previously thought necessary.

One embodiment of the storage solution addition step is shown in FIGS. 6, 7 and 8. Note, other component collection processes are not shown here (i.e., whether simultaneous or consecutive collection processes for other components (e.g., plasma and/or platelets) are used is not depicted or described here). In FIGS. 6,7 and 8, the collection bag 954 is shown attached to the upper hook 996 and the air bag 962 hung on another hook 998 (note, air bag 962 may not need to be hung from a hook but could have air bled thereto after the other steps in the process as suggested below). Then, a storage solution bag 970 can be hung from yet another hook 997 so that when connected and hung as shown in FIGS. 6 and 7, storage solution can flow down through tubing line 982 and through sterile barrier 986 through pump loop 142, connecting lines 146 and 952 and then through filter 960 and ultimately into collection bag 954. Although flow of both storage solution and RBCs is shown entering the filter 960 in the downward direction in FIGS. 6 and 7 and the upward direction in FIG. 8, it is also understood that flow to the filter 960 can be in any direction desired, including, but not limited to sideways. This flow against gravity is possible because the RBCs are pushed through the filter.

Alternatively, the embodiment shown in FIG. 7 also includes a depiction of the placement of the filter 960 in a substantially fixed position on device 6. In this embodiment flow will remain in a downward direction to aid in priming the filter 960. Clips or other restraining devices 901 are shown holding filter 960 in place. The further steps of having collected or simultaneously collecting components other than the RBCs in bag 954 and/or the alternatives of simultaneously pumping solution into the flow of RBCs and/or having completed filtration thereof through filter 960 prior to the addition of storage solution to filter 960 and bag 954 are not easily separately shown in the Figs.; however, flow control over the storage solution will preferably be made by a pump on device 6 engaging loop 142.

The embodiment shown in FIG. 8 depicts the filter 960 hanging from bag 954 without attachment to device 8. This embodiment allows flow of both storage solution and RBCs in the upward direction to and through the filter 960.

In either event, upon completion of all filtration and/or chasing with additive solution, the collection bag 954 may be separated from the rest of the set 8. Optional clamp 966 may be closed prior to such a separation. The separation may be made by RF sealing the tubing line 965 above the filter or line 952 below the filter and then separating in accordance with U.S. Pat. Nos. 5,345,070 and 5,520,218, inter alia, along the RF-sealed portion of the tubing line. Other well known methods can also be used to close the tubing line and then also separate the RBC collection system 950 from the remainder of the disposable assembly 8. An RBC collection system 950 which would be remaining after one such severing, e.g., below the filter 960, is shown schematically in FIGS. 4 and/or 5A or 5B (see below).

With respect to FIG. 4 it is noted that tubing line 965 may be a segmented tubing line that is further sealed to provide sample segments as is well known. It is also understood that tubing line 961 in addition to tubing line 965 or alternatively to tubing line 965 may also be segmented to again provide the desired samples for blood tying and other optional purposes.

The use of an optional two collection bag assembly 950a as shown in FIG. 5A or assembly 94b as shown in FIG. 5B is not much different from the above process. Pressure pushing to either bag 954 or 954a through filter 960 (or 960a) through each of the branch lines 965a, 964b could be used to fill both collection bags 954, 954a simultaneously, or one at a time (wherein a flow stopping member such as a clamp (966a or 966b) could be used to selectively arrest flow into first one then the other of bags 954, 954a until full). A double product could even be collected into just one of the two bags and then half that volume transferred to the other bags later. Then, however, when a desired double product is filtered and collected accordingly, it may be preferred to provide more control over the addition of product as well as the storage solution addition and/or flush process with manual clamps 966a and 966b, for example. First, it may be desirable to ensure that the two bags 954, 954a have substantially equal collected volumes, by weight or other means. Excess from one bag may be manipulated into the other bag, by hand compression for example, to flow through the adjoining tubing lines 965, 965a, or 965b. Then, it may be desired to deliver known amounts of storage solution into the respective bags 954a, 954b, via clamping first one tubing line 965a, 964b (using clamps 966a or 966b), and then the other during the flush or chase of storage solution through filter 960. Removal of air from the two collection bags into respective air bags 962, 962a would occur as with a single bag collection process. Note, the first alternative here, FIG. 5A, involves only a single filter 960 for processing the RBCs for both bags 954, 954a. However, a second filter 960a (shown in FIG. 5B) may alternatively be used herewith as well. As shown in FIG. 5B, separated RBCs could be made to flow through tubing line 952 and spur 952b through a first filter 960 into a first collection bag 954, either until this bag is filled, or simultaneously with flow from tube 952 split or diverted to flow through the alternative second tubing spur 952a and filter 960a to be collected in the second bag 954a. Other alternatives for double RBC product filtration will also be apparent.

Several advantages can be realized utilizing the preconnected disposable assembly and the above-described procedure for high-crit red blood cell collection and filtration. Such advantages include: consistency in final RBC product volume and hematocrit; reduced exposure of a recipient if multiple units of blood products are collected from a single donor and transfused to a single recipient; reduced time requirements for RBC collection and filtration, including collection of double units of red blood cells if desired, and reduced risks of bacterial and leukocyte contamination.

In the past there were various reasons why this high-hematocrit (high-Hct or high-crit) with storage solution (e.g., AS-3 or SAG-M) metered into the RBC flow and/or flushed after RBC filtration completion approach would not have appeared to work, and these include expected pressure problems of high hematocrit RBCs pushed through the filter 960 resulting in compromised cells; an expected risk of blocking the filter 960 with the high-crit RBCs; previously unknown leukodepletion levels at this high hematocrit under a push pressure; and the apparently likely "wash-out" or flushing of the WBCs by the storage solution (e.g., AS-3 or SAG-M) through a filter 960. Also red blood cell hemolysis or lysing was a contemplated potential problem.

It was conceived and determined to test for possible high-crit and/or storage solution diluted pushed filtration capabilities even though the prospect for success appeared unlikely at the outset. The results should overcome many negative expectations. For example, a diluted RBC product flowing through the filter may reduce the pressure drop (relative to undiluted RBCS) across the filter which would be advantageous to continuous flow particularly if used with an enhanced pressure push of this flow. A diluted RBC product achieves appropriate filtering during a shorter period of time than an undiluted RBC product. Even though an undiluted product may take a longer time period to filter than a diluted product it is noted that filtering either a diluted or undiluted product reduces the overall processing time as compared to post-collection filtration. By performing high-crit or even diluted pushed filtration immediately during the overall RBC separation and collection process, the resulting RBC product units are ready to be stored right from the machine without further processing. Fewer bags are used, and there are thus less handling requirements. Operator time is then freed up for performance of other procedures. Quality control may be simplified as well in that with pumped addition of additive solution, the quantity of solution added can be more tightly controlled so that a final hematocrit and percent recovery of the RBC product with additive solution added (calculations and/or weights) can be obtained easily by machine control and metering without the need for further human intervention and/or testing.

While one approach for RBC collection and filtration has been described above, other approaches will be apparent as well. For example, FIGS. 6 and 7 show alternate locations for the placement of the respective filter 960 relative to a blood component separation device 6. It is further noted that the filter may be mounted on alternative locations on the device 6. In particular, note the hanging bracket 900 hanging from hook 999. Bracket 900 may have one or more clamping members 901 which may be used to hold the filter 960 in a desired orientation throughout use on the machine 6. As shown, for example, a generally downward flow orientation may prove preferable, perhaps for example in initial priming.

The filter may also hang from bag 954 as shown in FIG. 8. This provides a generally upward flow orientation. Also, sidewards and other flow orientations could be used depending on the desired filter location.

Figure 9:
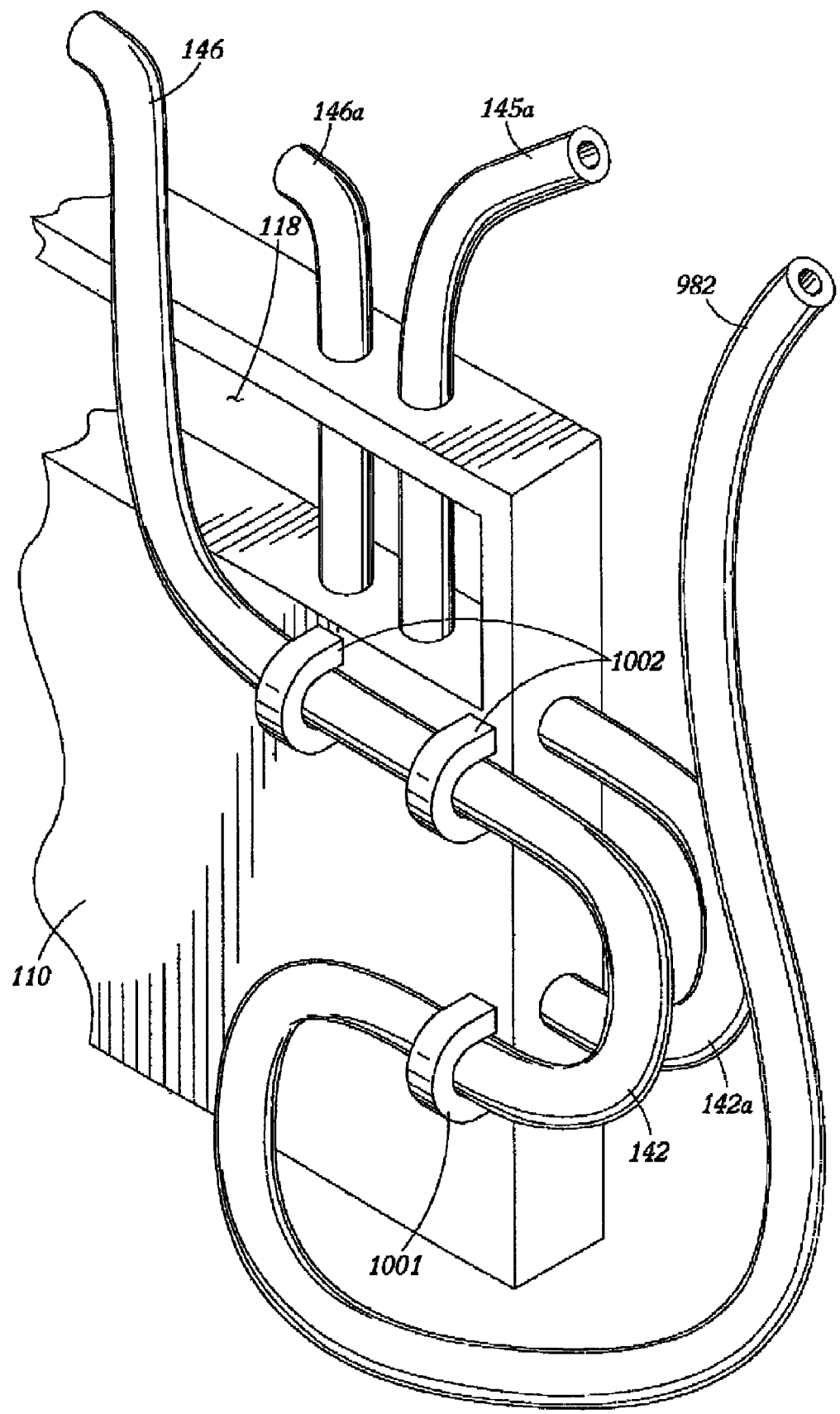
FIG. 9 is a partial isometric view of an alternative cassette assembly which may be used in a tubing and bag set such as that shown in FIGS. 1, 2 and 3.

Numerous further alternative elements and/or embodiments are available. For example, as depicted in FIG. 9, an additive solution tubing line 982 and loop 142 with connecting line 146 may be integrally connected to flow lines inside a cassette 110 (as suggested, but not required, by the embodiments of FIGS. 1-8); however, these elements may be added to the system either without a cassette, or attached to or run alongside a cassette 110. As shown in FIG. 9, a tubing line 982 (which is adapted to be connected to an additive solution source (not shown)), may be run to a cassette 110 and connected thereto in a fashion perhaps like that shown; e.g., using one or more connectors 1001, 1002. Principally, here, a connection is preferably formed to create a loop 142 which can be engaged by a pump on machine 6, and also to create a connecting member 146 which may similarly be engaged by a clamp/valve (not shown) also on machine 6. Notably, these members may all be formed from one length of tubing held in position such as shown. Also, these members could be manufactured together with cassette 110 and the other tubing elements or added post-manufacture thereto.

Further, note the other tubing loop 142a and the other extending tube portions 145a and 146a shown in FIG. 9. These additional elements, preferably disposed connected to interior flow channels in cassette 110 as suggested/shown by similar channels in FIGS. 2 and 3, e.g., are intended to depict an alternative additional functionality wherein a single peristaltic pumping device preferably of the double header type emanating from machine 6 may engage both the tubing loops 142 and 142a simultaneously to provide for pumping fluids through either or both of such loops, as may be desired.

As more fully described below, such tubing loops could also be used with respect to the plasma pump associated with loop 162.

With respect to FIG. 9, a single valve/clamp member (also not shown) could also be used to engage members 146 and 146a simultaneously to stop or allow flow through each of these at an appropriate time as well.

One possible use of such a set-up could include collecting platelets from vessel 352 and pumping these via tubing loop 142a to and through tubing extension 145a to a platelet collection container/bag (not shown). The valve/clamp member (not shown) of device 6 will then have extending tubes 146 and 146*a* clamped shut at this time so that no platelets will be returned to the donor and no additive solution will flow through line 146. Thus, in this embodiment, RBCs will either be simultaneously collected without dilution with additive solution which would then be flushed and added after platelet collection completion, or RBCs will not be collected until after platelet collection completion. In either event, when it is determined to flow additive solution through line 146, the valve/clamp member of device 6 is opened relative thereto (thereby, in this embodiment, simultaneously opening platelet flow through line 146*a* for return to the donor, and closing off line 145*a* to halt collection of platelets), and the pump engaging loops 142 and 142*a* can be activated to flow additive solution from the source, through line 982, loop 142 and extension 146 for connection to lines 951 and 952 (see FIGS. 2 and 3). Alternative valve/clamping and/or pumping scenarios could be used as well. For example, separate valves could be used for one or more of the extending members 146, 146*a* and/or 145*a*, thus allowing for more individualized control and perhaps metering of flows (e.g., a periodic or pulsatile flow could be desired/effected of additive solution through line 142, discrete from the flows through lines 145*a*, 146*a*). Also, a discrete additional additive solution pump in an ancillary system (not shown) could be used discrete from the dual pump header concept shown in FIGS. 9, and 12. Note, other systems other than active pumps may alternatively be used so long as the system establishes flow of the desired storage solution, and provision is made for a valve and/or a flow meter in order to provide for proportionate flow of the storage solution relative to the RBCs to yield a desirable final collected hematocrit. Note, this final hematocrit could be as low as 40 or even lower, as may be desired by the end user.

Figure 10:
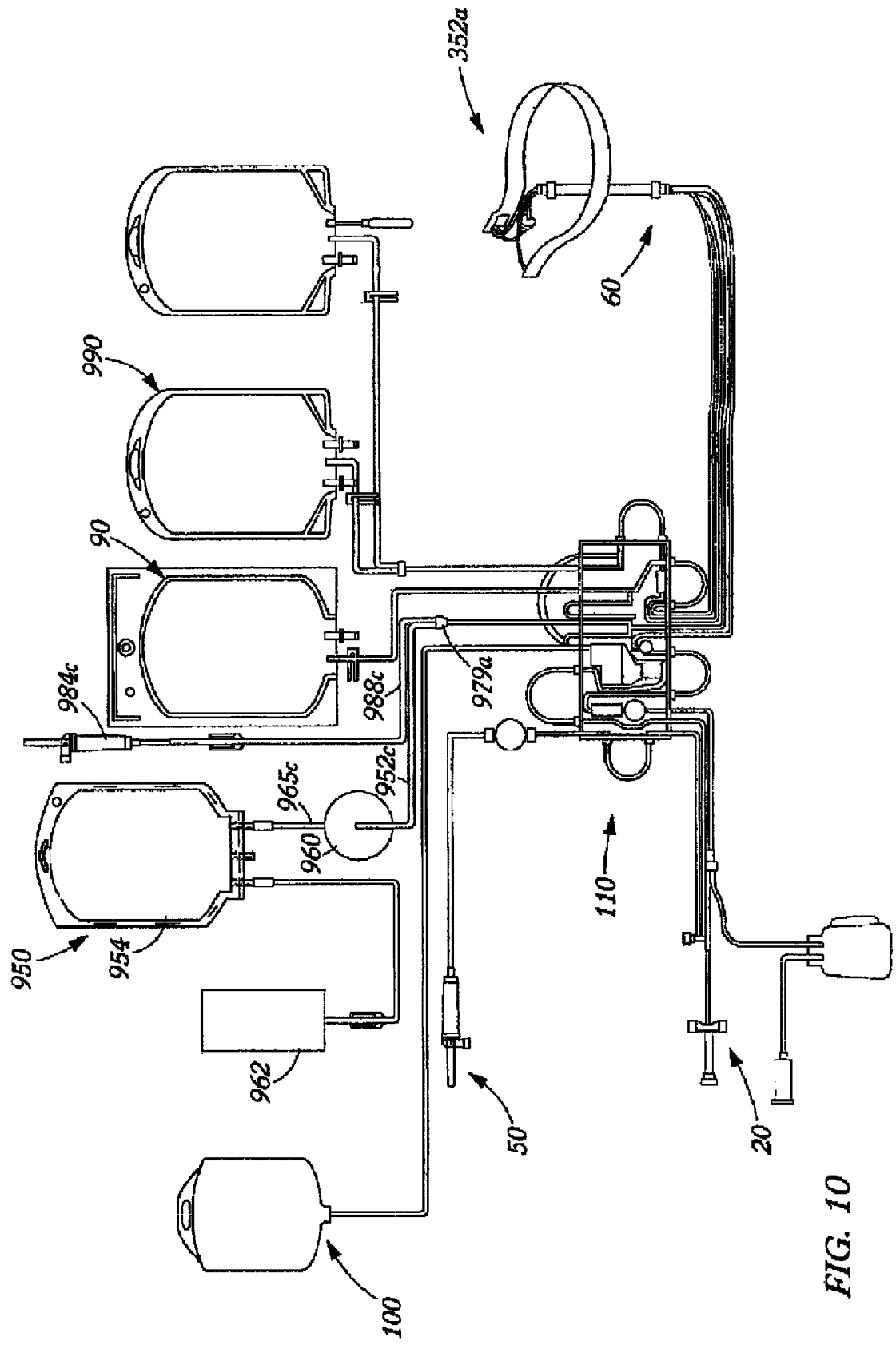
FIG. 10 illustrates a tubing and bag set similar to FIG. 2 but with an alternative blood processing vessel and storage or additive solution assembly.

A further embodiment for the addition of the additive/storage solution is shown in FIG. 10. This embodiment also shows an alternative blood processing vessel 352*a* found in the Trima® Accel™ apheresis system described above. More details of this "single stage" blood processing vessel can be found in U.S. Pat. Nos. 6,053,856 and 6,334,842 assigned to the same assignee as the instant invention.

The additive/storage solution system of FIG. 10 is of the gravity feed type. In the embodiment of FIG. 10 like numerals are used for the assemblies or circuits common with the embodiment of FIG. 2. Spike or needle 984*c* of FIG. 10 is adapted for attachment to an additive/storage solution container by methods as described with respect to FIG. 3. Additive/storage solution may be provided through inlet line 988*c* through connector 979*c* to join the RBC product in filter inlet line 952*c*. Again the additive/storage solution can be provided after filtration to displace any RBCs remaining in the filter as described above. Filtered RBCs and any storage solution used are collected through line 965*c* into bag 954. In the embodiment of FIG. 10 it is understood that the RBCs are filtered in the high-crit state. It is also understood that other components such as plasma or platelets can also be optionally collected if desired into the bags or containers of system 990. The embodiment of FIG. 10 does not require pumping for the addition of the additive/storage solution as such solution can be gravity drained resulting in an overall more simplified structure.

Figure 11:
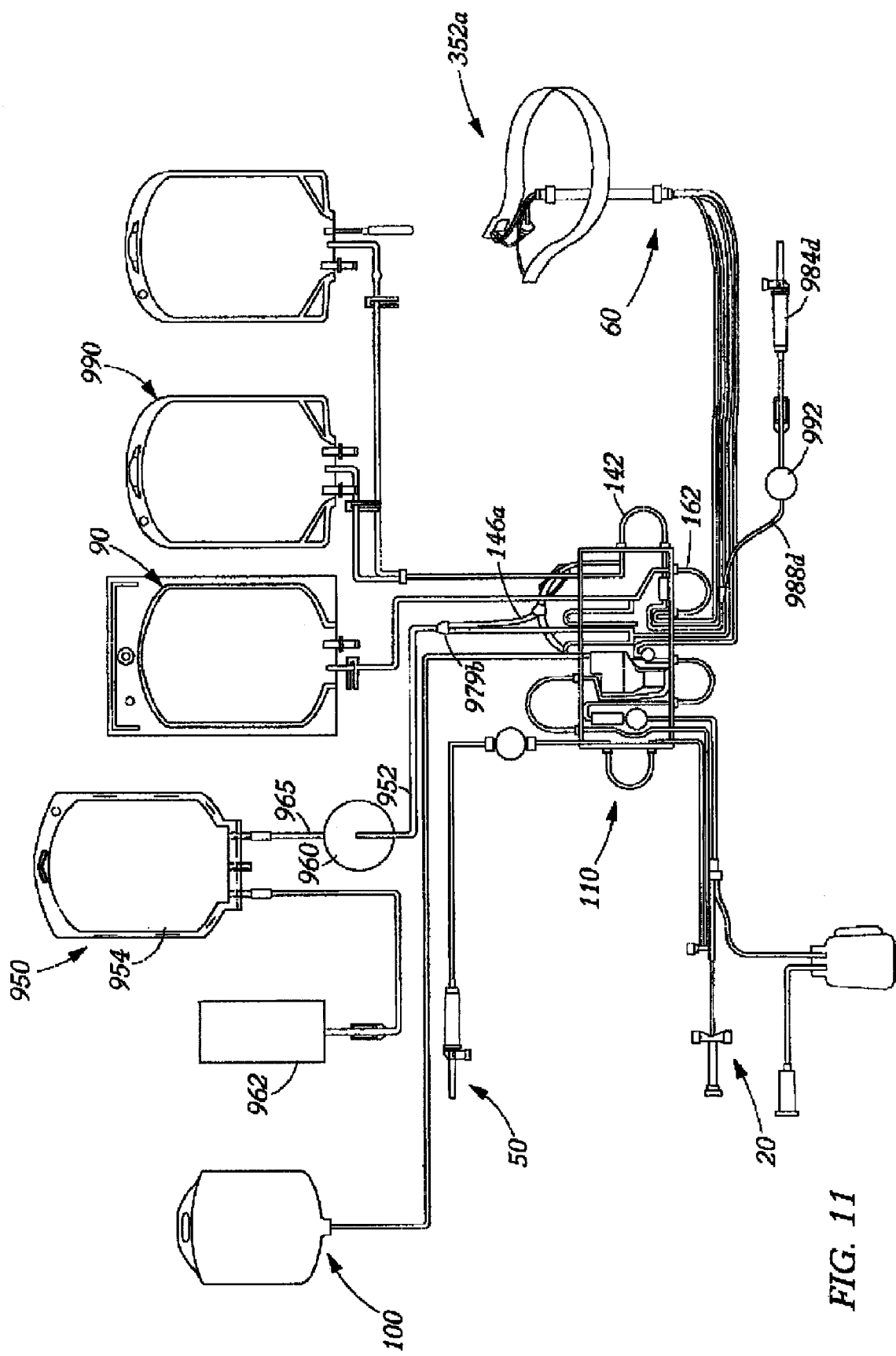
FIG. 11 illustrates a tubing and bag set similar to FIG. 10 but with an alternative storage or additive solution assembly.

FIG. 11 illustrates a further option for providing the desired amount of storage/additive solution to a system similar to that of FIG. 2, but using the blood processing vessel described in FIG. 10.

In the embodiment of FIG. 11 storage/additive solution is provided through spike 984*d* to line 988*d*. A fluid detector or flow meter 992 monitors the addition of the additive/storage solution to assure that the desired amount is added to the RBCs. From line 988*d* the storage/additive solution is pumped through loop 142 to lines 146*a* and 952 and thus through filter 960. Again it is understood that additive/storage solution may flow through filter 960 after collection to displace residual RBCs from the filter. Again the RBCs are filtered in the high-crit mode although it is understood that the system could also be adapted for a diluted fitration mode. The disposable of FIG. 11 also allows for the optional collection of additional components such as plasma or platelets into the bags or containers of system 990.

Figure 12:
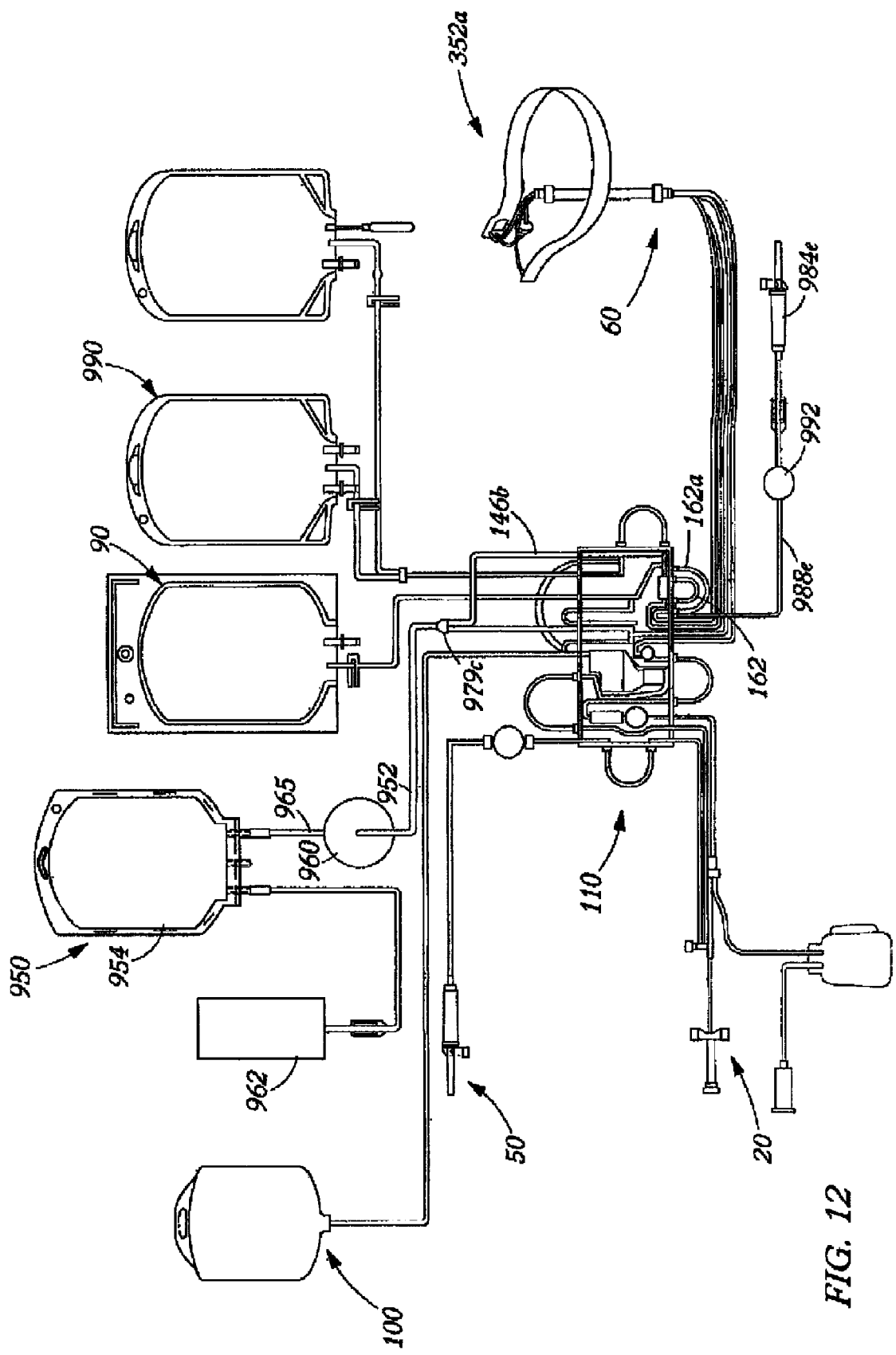
FIG. 12 illustrates a system similar to FIGS. 10 and 11 but with another alternative storage or additive solution assembly.

An additional alternative embodiment for provision of additive/storage solution is shown in FIG. 12. Again blood processing vessel 352*a* and optional additional component collection system 990 is shown. In this embodiment the plasma pump is a double header pump as described above with respect to FIG. 9. Storage/additive solution may be provided through spike 984*e* and line 988*e* (having optional fluid detector/flow meter 992) through tubing loop 162*a*, line 146*b*, connector 979*c* to filter line inlet 952. As in the embodiments of FIGS. 10 and 11, the additive/storage solution may be provided at the appropriate time for filtering a diluted or undiluted product. Again it is preferable that an amount of additive/storage solution displace residual RBCs in the filter at the end of the collection.

It is noted that a double header pump may also be used with tubing loop 162 and tubing loop 162*a* for plasma collection if desired. The valving options for double pump loops as well as the attachment options as described with respect to FIG. 9 above may also be used. Also, an additional valve can optionally be provided in window 118. Other alternatives include the use of existing valves for the additional tubing or the use of a manual clamp. In this embodiment the storage/additive solution can flow through tubing attached to cassette 110 as described in FIG. 9 or it can flow optionally through a channel in the cassette 110.

Figure 13:
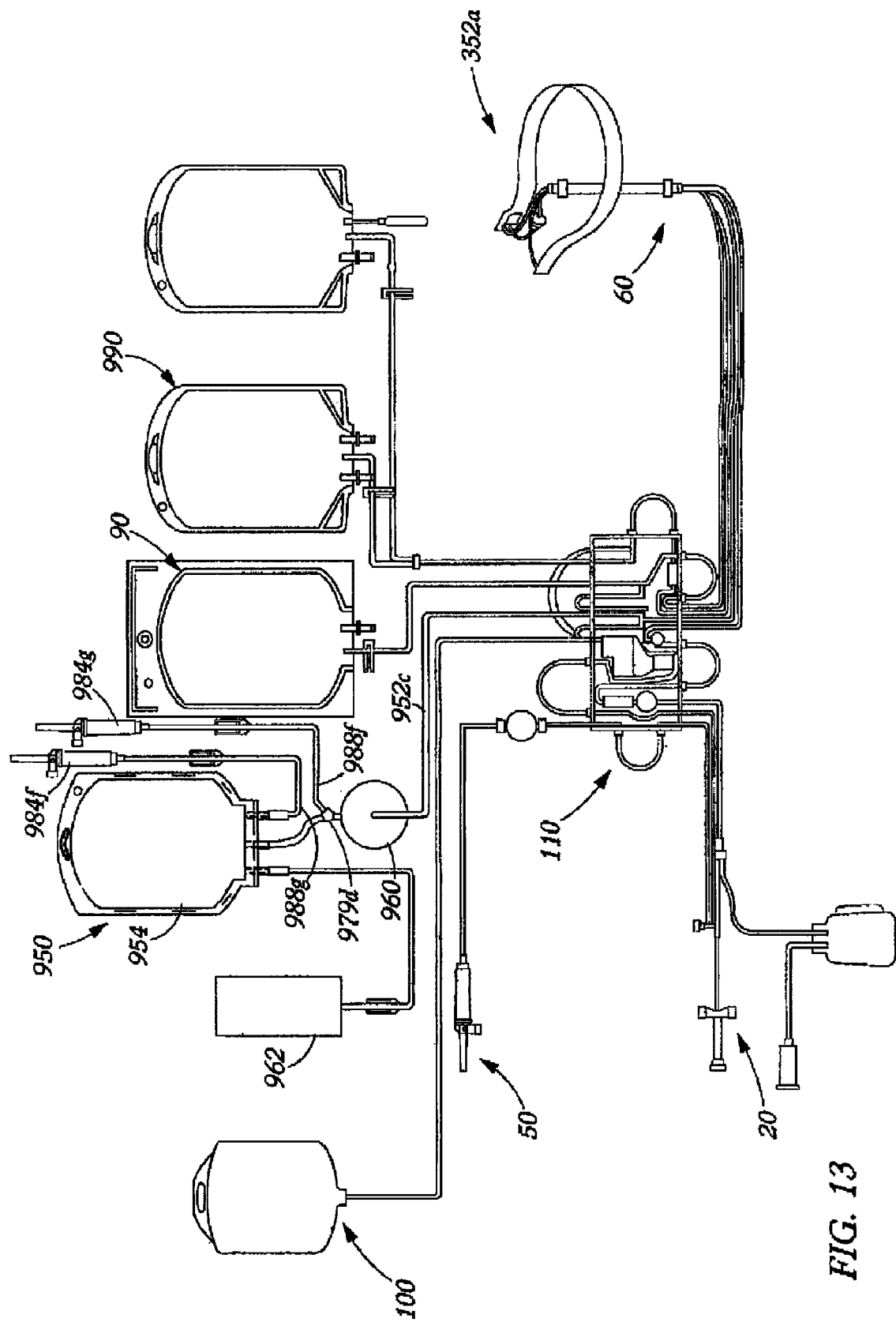
FIG. 13 illustrates yet another system similar to FIG. 10 but with another alternative storage or additive solution assembly and an additional saline solution assembly.

FIG. 13 is an embodiment similar to FIG. 10 in that the storage solution provided through spike 984*f* flows through line 988*g* to collection bag 954 by a gravity drain without the need for a pump. In this embodiment however the storage solution is not used to recover RBCs from the filter. In this embodiment, as can be seen in FIG. 13, the storage solution is provided directly to the collection bag for mixing with the already filtered RBCs. An additional spike 984*g* or bag of saline is provided. The saline flows through tubing 988*f*, connector 979*d* to tubing 965. The saline is then used to displace the volume of the filter and tubing such as 952*c* back to the cassette system 110 for return to the donor. In this embodiment it is understood that the storage solution and saline bags can be preconnected to the RBC collection assembly 950 or that such bags may be sterilely connected using the spikes with sterile barrier filters, (not shown) or other methods described above.

In order to assist an operator in performing the various steps of the protocol being used in an apheresis procedure with the apheresis system 2, the apheresis system 2 preferably includes a computer graphical interface 660 as illustrated generally in FIG. 1. The graphical interface 660 may preferably include a computer display 664 which has "touch screen" capabilities; however, other appropriate input devices (e.g., keyboard) may also be utilized alone or in combination with the touch screen. The graphics interface 660 may provide a number of advantages, but may preferably, at least, assist the operator by providing pictorials of how and/or when the operator may accomplish at least certain steps of the apheresis and/or filtration procedures.

For example, the display screen optionally may sequentially display a number of pictorials to the operator to convey the steps which should be completed to accomplish the filtering procedure described here. More particularly, a pictorial image optionally may be shown on the screen to pictorially convey to the operator when and/or how to hang the respective RBC and solution bags 954 and/or 970 on the machine 6, initially and/or during use with a storage solution dilution and/or flush (see FIGS. 6 and 7, for example). One or more pictorials may also be provided to instruct the operator when to open or close clamps to begin the filtration process, and/or to visually ensure that the filtration process has appropriately begun simultaneously or during RBC collection. One or more pictorials may also be used to instruct the operator when to connect the spike assembly 980 to a storage solution container 970 and/or when to open a clamp or break a frangible connector (if included) after and/or during the RBCs flow through filter 960, to thus initiate the flow of the storage solution through the filter 960 and flush any residual RBCs therethrough. One or more pictorials may also be used to instruct the operator when the tube line 965 leading to the RBC collection bag 954 should be sealed such that the RBC collect bag 954, and the remaining elements of RBC storage assembly 950 may be separated and/or removed from the disposable assembly 8/10 and/or from the device 6. A similar pictorial can instruct when to seal the air tube 961 to isolate the RBC collection bag 954 from the air bag 962 and the rest of the system after the filtration and flushing and air handling procedures may be completed.

Note, a further advantage of the presently described system includes the manner of handling air. More specifically, the present invention eliminates the prior need for the vents and/or by-pass methods and/or apparatuses of conventional red blood cell filters. Moreover, the present invention is capable of delivering this advantage with no reduction in and/or perhaps an increase in the recovery of RBCs that historically have been trapped inside the filtration device.

A means used by the present invention to deliver this advantage is through the provision of a storage solution flush through the filter 960 after the RBCs have finished filtering therethrough. The storage solution may then be able to wash RBCs caught therein out of the filter and then into the collection bag 954. Prior devices relied upon vents or by-pass mechanisms to assist in pushing out any RBCs disposed in the filter. Note, though not preferred or needed, vents or by-passes could still be used with the current pushed filtration process, and also with and/or in lieu of the storage solution flush after filtration. Thus such vents or by-passes may be optional features to the described system if it is desired to purge the filter 960 with air or with a combination of air and fluid.

In any event, elimination of the need for vents or by-passes also reduces other prior difficulties such as inadvertent allowances of excess air into the system. Extra air in the present system will not stop or slow the flow of blood or storage solution through the filter in the present invention. The extra air will then be caught within the collection bag 954 and may thus be removed at the end of the overall process to the air bag 962 (air moved thereto by bag positioning or squeezing, etc.). Then, also, because neither vents nor by-passes are required in the preferred embodiments here failures with respect to the operation of such vents are not of concern since the preferred subsequent storage solution flush recovers the RBCs from the filter without the previously desired use of a vent or by-pass. Consequently, also, the filter may be disposed at any of a plurality of alternative vertical dispositions above or below the vessel 352 and/or the collection bag 954. Operation of the present invention should not be hindered by such alternative placements. It is understood, however, that air could also be used to chase either the RBCs or additive solution through filter 960 as described above.

Although the instant invention eliminates the need for by-passes it is understood that one could be provided in the extracorporeal tubing circuit to by-pass the filter 960 in the event the leukoreduction is terminated or is not desired. Similarly it is understood that an optional pressure relief valve or vent could be added to prevent pressure build up in parts of the system including the filter.

The volume of storage solution to be used may, however, be modified depending upon the relative lengths of tubing lines used and/or the air that gets into the system. For example, if 100 ml of storage solution is desired to be mixed with the end product RBCs in collection bag 954 then some certain volume more than 100 ml of storage solution would preferably be fed into the system to compensate for the tubing lengths and the volume of the filter. The amount of solution may be chosen such that 100 ml would go into the collection bag 954 with the additional amount remaining in the tubing line and filter between the cassette 110 and the collection bag 954.

Note, a storage solution dilution during RBC filtration and/or flush after filtration completion are the primary alternatives taught here. However it is possible that storage solution flow into bag 954 may be begun at other times as well as, for example, prior to starting the high-crit or diluted RBC pushed filtration. Pulsed and/or intermittent flows may also be desirable to assist in removing final volumes of RBCs from the filter 960. A further alternative, although not preferred, may involve the use of retrograde flow of a fluid (air, plasma, saline, or additive solution) after removal of the collection bag 954, then flowing this additional fluid backwardly through the filter so that any trapped components can be flushed back to the cassette 110, and perhaps then flushed back to the donor 4.

Another alternative introduced hereinabove involves the use of alternative extracorporeal blood processing systems. Although the preference is for a continuous flow apheresis system, as described here, which includes returning some components back to the donor, batch flow and non-return systems are also useable herewith. For example, a batch mode processor takes in a certain quantity of whole blood, separates the blood into components (in a centrifuge bowl, e.g.) and then passes the separated components to collection containers or back to the donor. The filtration process of the present invention could foreseeably nevertheless operate in substantially the same manner such that the separated RBCs would nonetheless exist in a substantially high hematocrit state as they are flowed from the separation mechanism, at which point these high-crit separated RBCs could be flowed to a junction with a storage solution tubing line and from there be passed directly or soon thereafter to and through a filter 960 to be collected ultimately in a collection bag 954. Though continuity may be reduced (or substantially removed), the principles of pushed filtration (high-crit or diluted) during or soon after the overall separation and collection remain the same. Note, even if flow through the filter 960 stops at any point, or a plurality of points, this does not appear problematic here where any air entry therein is handled by ultimate capture in the air bag 962.

Smaller scale separation and collection devices are also envisioned to be useful herewith. For example, various separation devices (whether centrifugal or membrane or other types) are designed to separate only RBCs and plasma (with the remainder usually remaining in the RBC product), and these can take on smaller scale mechanizations. Nevertheless, the present invention is useful herewith as well in that RBCs separated hereby may also be freshly push-filtered at high and/or diluted hematocrits. The principle of push-filtering such RBCs during or soon after the overall separation and collection process remains the same here as well. Thus, whether continuous or in batch mode, a flow of high-crit or diluted, freshly-separated RBCs can be push-flowed from the separation device immediately or soon after previous processing therein, to and through filter 960 to a collection bag 954.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

The invention claimed is:

1. A disposable assembly for a blood processing system for separating blood into at least one component for collection and for the filtration of the blood component; said disposable assembly comprising:
   a blood removal assembly for removing blood from a donor/patient;
   a rotating blood processing vessel removeable interfitted within a rotatable centrifuge interconnected to said blood removal assembly, and coactive with the rotatable centrifuge for separating blood received from the donor/patient into blood components by centrifugation;
   a blood component collection assembly interconnected to said blood processing vessel, comprising:
      a leukoreduction filter pre-connected to said blood processing vessel and disposed to receive a blood component from said blood processing vessel; and
      a blood component collection container pre-connected to said filter;
   whereby said blood component collection assembly provides for the pushing of said blood component through the filter simultaneously with or during the overall continuous separation process; and collecting the blood component in the collection container after the pushing of said blood component through the filter.

2. A disposable assembly according to claim 1 wherein the collection assembly further provides for flowing a solution from a discrete storage solution bag through the filter after the completed pushing of the blood component through the filter; and collecting said solution in said blood component collection container for mixing with said blood component.

3. A disposable assembly according to claim 2 wherein the solution flows through the filter during the pushing of the blood component through the filter thereby mixing the solution with said blood component and said solution and said blood component are collected in said blood component collection container.

4. The disposable assembly of claim 1 further comprising:
   a discrete storage solution container;
   a first tubing line interconnected between said storage solution container and said blood component collection container; and
   a clamp in said first tubing line for allowing said first tubing line to be opened for the passage of storage solution through said first tubing line to said blood component collection container.

5. The disposable assembly of claim 1 further comprising:
   a first tubing line interconnected to said blood component collection container, said first tubing line being selectively connectable to a storage solution container; and
   a spike connector in said first tubing line for allowing said first tubing line to be connected to said storage solution container to provide for the passage of storage solution therethrough.

6. The disposable assembly of claim 1 further comprising:
   a first tubing line interconnected to said blood component collection container, said first tubing line being selectively connectable to a storage solution container; and
   said first tubing line having a pump loop formed therein for allowing said first tubing line to be engaged with a pump to provide for pumping storage solution therethrough.

7. The disposable assembly of claim 1 further comprising:
   an air removal bag interconnected to said blood component collection container for receiving air from said blood component collection container.

8. A disposable assembly according to claim 1 in which the blood component collection container is a first blood component collection container and wherein said blood component collection assembly further comprises a second blood component collection container and a second filter, said second filter being disposed in communication with said second blood component collection container; the disposable assembly further providing for passing the separated blood components from said separation system into and through said first filter firstly into the first blood component collection container, and then secondly through said second filter into the second blood component collection reservoir.

9. The disposable assembly of claim 1 comprising:
   a platelet collection bag interconnected to said blood component collection assembly for receiving separated platelets when platelets are to be collected.

10. The disposable assembly of claim 1 comprising:
    a plasma collection bag interconnected to said blood component collection assembly when plasma is to be collected.

11. The disposable assembly of claim 1 comprising:
    a cassette assembly interconnected to and between said blood removal, said blood processing vessel and said blood component collection assembly; said cassette assembly comprising integral fluid passageways for the passage of blood and blood components therethrough.

12. A disposable assembly for a blood processing system for separating blood into at least one component for collection and for the filtration of the blood component; said disposable assembly comprising:
    a blood removal assembly for removing blood from a donor/patient;
    a blood processing vessel interconnected to said blood removal assembly, and coactive with a separation system for separating blood received from the donor/patient into blood components;
    a blood component collection assembly interconnected to said blood processing vessel, comprising:
       a leukoreduction filter pre-connected to said blood processing vessel and disposed to receive a blood component from said blood processing vessel; and
    a blood component collection container pre-connected to said filter;

whereby said blood component collection assembly provides for the pushing of said blood component through the filter simultaneously with or during the overall continuous separation process; and collecting the blood component in the collection container after the pushing of said blood component through the filter;

and wherein said blood component collection assembly further comprises a second blood component collection container and a second leukoreduction filter, said second filter being disposed in communication with said second blood component collection container;

the disposable assembly further providing for passing the separated blood components from said separation system into and through said first and second filters simultaneously and thus simultaneously into the first and second blood component collection containers.

* * * * *